United States Patent
Kannan et al.

(10) Patent No.: US 10,317,400 B2
(45) Date of Patent: Jun. 11, 2019

(54) AU MULTICOMPONENT NANOMATERIALS AND SYNTHESIS METHODS

(71) Applicant: The Curators of the University of Missouri, Columbia, MO (US)

(72) Inventors: Raghuraman Kannan, Columbia, MO (US); Ajit Zambre, Columbia, MO (US); Anandhi Upendran, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 0 days.

(21) Appl. No.: 15/109,058

(22) PCT Filed: Dec. 23, 2014

(86) PCT No.: PCT/US2014/072092
§ 371 (c)(1),
(2) Date: Jun. 29, 2016

(87) PCT Pub. No.: WO2015/103028
PCT Pub. Date: Jul. 9, 2015

(65) Prior Publication Data
US 2017/0168045 A1    Jun. 15, 2017

Related U.S. Application Data

(60) Provisional application No. 61/964,285, filed on Dec. 30, 2013.

(51) Int. Cl.
*A61K 51/12* (2006.01)
*B82Y 30/00* (2011.01)
(Continued)

(52) U.S. Cl.
CPC ... *G01N 33/54346* (2013.01); *A61K 51/1244* (2013.01); *C07K 17/14* (2013.01);
(Continued)

(58) Field of Classification Search
None
See application file for complete search history.

(56) References Cited

U.S. PATENT DOCUMENTS

2006/0222595 A1    10/2006  Mukherjee et al.
2015/0231285 A1*   8/2015   Wang ............... A61K 51/088
                                                    424/9.2

FOREIGN PATENT DOCUMENTS

WO    WO 2011151631 A1 * 12/2011 ......... A61K 49/0002
WO    WO-2013142200 A1 *  9/2013 ............... C07K 7/08

OTHER PUBLICATIONS

A Zambre, F Silva, A Upendran, Z Afrasiabi, Y Xin, A Paulo, R Kannan. "Synthesis and characterization of functional multicomponent nanosized gallium chelated gold crystals." Chemical Communications, vol. 50, 2014, pp. 3281-3284.*

(Continued)

Primary Examiner — Isaac Shomer
(74) Attorney, Agent, or Firm — Greer, Burns & Crain, Ltd.; Steven P. Fallon

(57) ABSTRACT

A multicomponent nanomaterial AuNP(DTDTPA)(Ga), where DTDTPA is an amino-carboxylate ligand (diethylene triamine pentaacetic acid, DTPA) linked to the surface of the Au nanoparticle (NP) via dithiol (DT) linkage. Another embodiment is a multicomponent nanomaterial AuNP(DT-DTPA)(Ga) with a biomolecule attached. In preferred embodiments, the Ga is Ga-67 or Ga-68. Preferred synthesis methods are conducted at room temperature.

8 Claims, 19 Drawing Sheets
Specification includes a Sequence Listing.

(51) Int. Cl.
*B82Y 40/00* (2011.01)
*C07K 17/14* (2006.01)
*C12N 11/14* (2006.01)
*G01N 33/543* (2006.01)
*G01N 33/58* (2006.01)

(52) U.S. Cl.
CPC ........... *C12N 11/14* (2013.01); *G01N 33/587* (2013.01); *B82Y 30/00* (2013.01); *B82Y 40/00* (2013.01); *Y10S 977/773* (2013.01)

(56) References Cited

OTHER PUBLICATIONS

C Alric, J Taleb, G Le Duc, C Mandon, C Billotey, Al Meur-Herland, T Brochard, F Vocanson, M Janier, P Perriat, S Roux, O Tillement. "Gadolinium Chelate Coated Gold Nanoparticles as Contrast Agents for Both X-ray Computed Tomography and Magnetic Resonance Imaging." Journal of the American Chemical Society, vol. 130, 2008, pp. 5908-5915.*
Author Unknown, "Gadolinium: Questions and Answers in MRI." http://mriquestions.com/whygadolinium.html, accessed by examiner on May 8, 2017, 2 printed pages.*
PJ Debouttiere, S Roux, F Vocanson, C Billotey, O Beuf, A Favre-Reguillon, Y Lin, S Pellet-Rostaing, R Lamartine, P Perriat, O Tillement. "Design of Gold Nanoparticles for Magnetic Resonance Imaging." Advanced Functional Materials, vol. 16, 2006, pp. 2330-2339.*
Cutler, et al., "In Vivo Evaluation of Multifunctional DTDTPA Gold Nanoparticles for Molecular Imaging", World Journal of Nuclear Medicine, vol. 12. Suppl. 1, Feb. 1, 2013, pp. 1-188.*
N Gonzalez, TW Moody, H Igarashi, T Ito, RT Jensen. "Bombesin-related peptides and their receptors: recent advances in their role in physiology and disease states." Current Opinion in Endocrinology, Diabetes, and Obesity, vol. 15, 2008, pp. 58-64. (Year: 2008).*
D Suresh, A Zambre, N Chanda, TJ Hoffman, CJ Smith, JD Robertson, R Kannan. "Bombesin Peptide Conjugated Gold Nanocages Internalize via Clathrin Mediated Endocytosis." Bioconjugate Chemistry, vol. 25, 2014, pp. 1565-1579, available online Jul. 14, 2014. (Year: 2014).*
Tsoukalas et al., "Initial in vitro and in vivo assessment of Au@DTDTPA-RGD nanoparticles labeled with Ga-68" Annual Meeting Sep. 1-Sep. 3, 2013. (Year: 2013).*
F Ciardiello, G Tortora. "A Novel Approach in the Treatment of Cancer: Targeting the Epidermal Growth Factor Receptor." Clinical Cancer Research, vol. 7, Oct. 2001, pp. 2958-2970. (Year: 2001).*
BA Nock, A Nikolopoulou, A Galanis, P Cordopatis, B Waser, J-C Reubi, T Maina. "Potent Bombesin-like Peptides for GRP-Receptor Targeting of Tumors with 99mTc: A Preclinical Study" Journal of Medicinal Chemistry, vol. 48, pp. 100-110 (Year:2005).*
Alric, Christophe, et al., "Gadolinium Chelate Coated Gold Nanoparticles as Contrast Agents for Both X-ray Computed Tomography and Magnetic Resonance Imaging", J. Am. Chem. Soc., 130 (18), (2008), pp. 5908-5915.
Debouttiere et al., "Design of Gold Nanoparticles for Magnetic Resonance Imaging", Advanced Functional Vlaterials, vol. 16, Iss. 18., Nov. 3, 20016, pp. 2330-2339.
Maecke et al.,"68Ga-Labeled Peptides in Tumor Imaging", The Journal of Nuclear Medicine, vol. 46, No. 01, Jan. 1, 2005, pp. 172S-178S.
Valk et al., "Positron Emission Tomography: Basic Science and Clinical Practice", (Oct. 2004), p. 255. Article retrieved from the Internet<https://books.google.com/books?id= svliBnNd2LcC&pg=PA255&1pg=PA255&dq=gallium+biomolecule+and+dTpa&source> on May 3, 2015.
Welinder, K.G., "Covalent structure of the glycoprotein horseradish peroxidase (EC 1.11.1.7)", FEBS Letters, vol. 72, No. 1, (Dec. 1976), pp. 19-23.
Yazdanpanah et al., "Gallium-driven assembly of gold nanowire networks", Applied Physicas Letters, vol. 85, No. 39, Aug. 30, 2004, pp. 1592-1594.
Zambre et al., "Synthesis and characterization of functional multicomponent nanosized gallium chelated gold crystals", Chemical Communications, vol. 50, Jan. 13, 2014 (Jan. 13, 2014), pp. 3281-3284.
Cost TD1004 Action—Theranostics Imaging and Therapy: An Action to Develop Novel Nanosized Systems for Imaging-Guided Drug Delivery, Annual Meeting—Sep. 1-Sep. 3, 2013, Meeting Venue: Hotel Stratos Jassilikos, Athens, Greece.
Tsoukalas et al., "Initial in vitro and in vivo assessment of Au@DTDTPA-RGD nanoparticles labeled with Ga-68", Cost TD1004 Action "Theranostics Imaging and Therapy: An Action to Develop Novel Nanosized Systems for Imaging-Guided Drug Delivery"; Annual Meeting Sep. 1-Sep. 3, 2013. Meeting Venue: Hotel Stratos Jassilikos, Athens Greece, Sep. 1, 2013, p. 35, XP055368554, Hotel Stratos Vassilikos, Athens, Greece.

\* cited by examiner

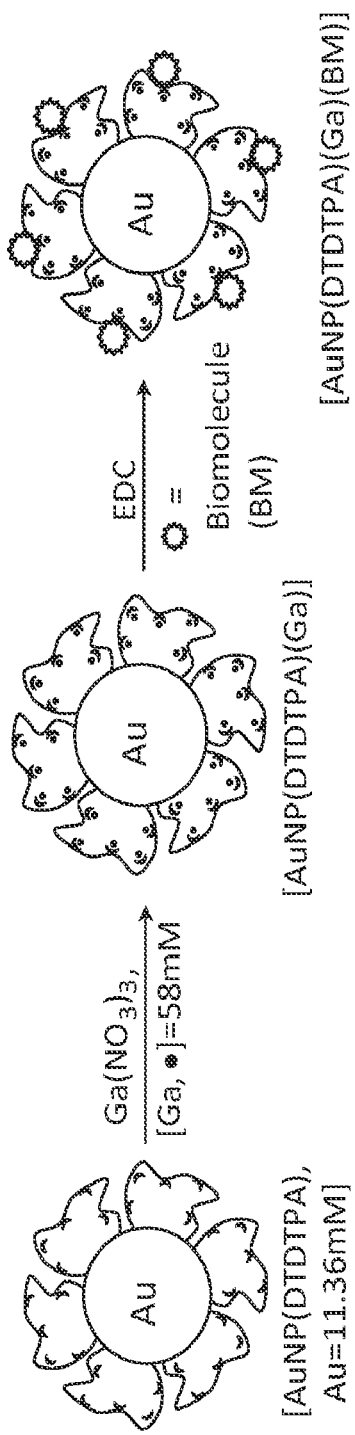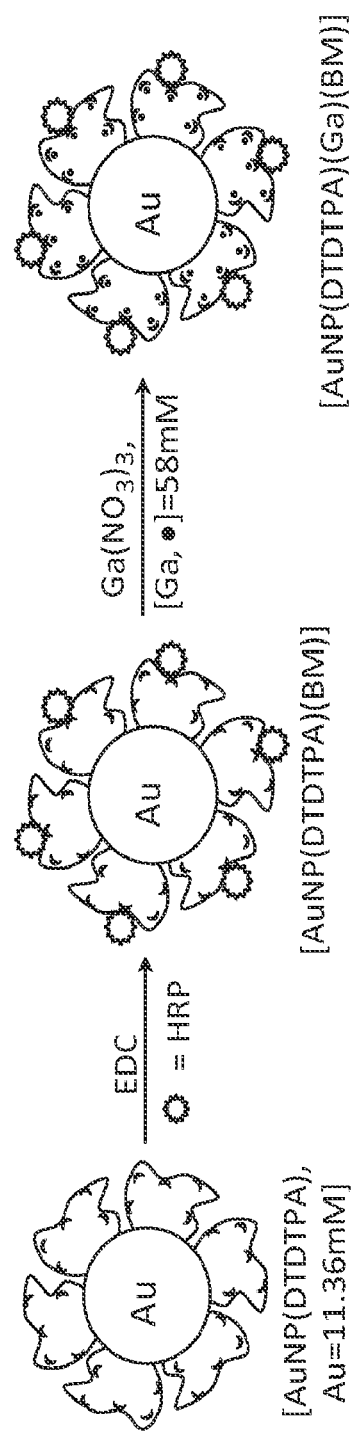
FIG. 2A
FIG. 2B

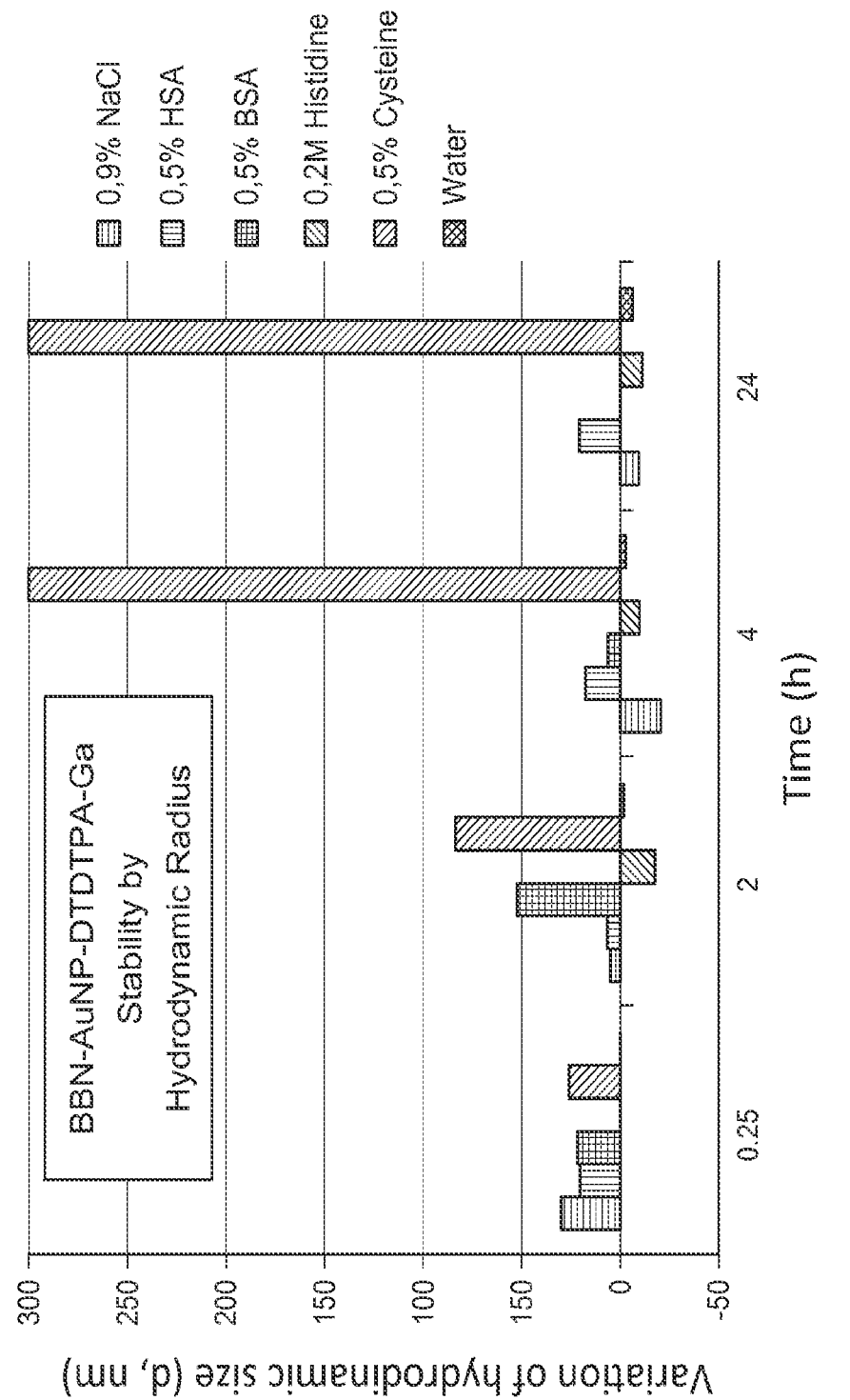

SEQUENCE LISTING

```
<160> NUMBER OF SEQ ID NOS: 2

<210> SEQ ID NO 1
<211> LENGTH: 8
<212> TYPE: PRT
<213> ORGANISM: Artificial Sequence
<220> FEATURE:
<223> OTHER INFORMATION: Ligand
<220> FEATURE:
<221> NAME/KEY: Modified
<222> LOCATION: (5)..(5)
<223> OTHER INFORMATION: Lipoic acid is attached to the peptide by
      forming amide bond between carboxylic group of lipoic acid and
      amine of glutamine.

<400> SEQUENCE: 1

Gln Trp Ala Val Gly His Leu Met
1               5

<210> SEQ ID NO 2
<211> LENGTH: 15
<212> TYPE: PRT
<213> ORGANISM: Artificial Sequence
<220> FEATURE:
<223> OTHER INFORMATION: Ligand
<220> FEATURE:
<221> NAME/KEY: Modified
<222> LOCATION: (1)..(1)
<223> OTHER INFORMATION: Lipoic acid is attached to the peptide by
      forming amide bond between carboxylic group of lipoic acid and
      amine of the first lysine.
<220> FEATURE:
<221> NAME/KEY: Modified
<222> LOCATION: (1)..(4)
<223> OTHER INFORMATION: Di- polyethylene glycol is attached to the
      tyrosine residue of the peptide and lysine residue
<220> FEATURE:
<221> NAME/KEY: Modified
<222> LOCATION: (1)..(3)
<223> OTHER INFORMATION: 1,4,7,10-tetraazacyclododecane-1,4,7,10-
      tetraacetic acid is attached to the peptide via amide linkage to
``` one of the lysine residues

<400> SEQUENCE: 2

Lys Lys Lys Tyr His Trp Tyr Gly Tyr Thr Pro Gln Asn Val Ile
1               5                   10                  15

AU MULTICOMPONENT NANOMATERIALS AND SYNTHESIS METHODS

PRIORITY CLAIM AND REFERENCE TO RELATED APPLICATION

The application claims priority under 35 U.S.C. § 119 from prior provisional application Ser. No. 61/964,285, which was filed Dec. 30, 2013.

FIELD

A field of the invention is composite nanomaterials. Example applications of the invention include biomedical applications such as disease treatment and disease detection.

REFERENCE TO SEQUENCE LISTING

This application comprises a sequence listing text file, named 559456.TXT, created Aug. 10, 2016 of 1477 bytes in size. The sequence listing is incorporated herein by reference.

BACKGROUND

Multicomponent nanomaterials combine physical and biological properties of multiple materials within a single nanoconstruct. Multicomponent nanomaterials provide unique opportunities to combine properties offered separately into a single nanoconstruct. These opportunities can expand applications of a nanomaterials, such as providing simultaneous detection and treatment of various human diseases. Combining multiple components within a single nanomaterial poses significant synthesis challenges. Many efforts to combine different materials into a single nanomaterial result in the loss of one or more desired properties of the individual materials.

AuNP-DTDTPA has been conjugated with Gd, In, or $^{99m}$Tc, and these elements have excellent molecular imaging capabilities. R. Zirbs, F. Kienberger, P. Hinterdorfer and W. H. Binder, Langmuir, "Directed assembly of Au nanoparticles onto planar surfaces via multiple hydrogen bonds," 21, 8414-8421 (2005). This technique involved directed, specific molecular interactions to bind the particles to a monolayer surface. The surface was prepared with receptors, and Au nanoparticles covered with the matching barbituric acid receptors bound with high selectivity onto this surface by a self-assembly process mediated by multiple hydrogen bonds. The binding mechanism is highly specific. Dithiolated DTPA (DTDTPA) provides both soft N-donor and hard O-donor ligands. Unlike other N, O-ligands, DTPA forms kinetically inert and thermodynamically stable metal complexes under normal laboratory conditions. DTPA based metal chelates have shown excellent in vivo stability. F. N. Weizer V G, "The interaction of gold with gallium arsenide" Journal of Applied Physics, 1988, 64, 4618-4623. See, C. Alric, J. Taleb, G. Le Duc, C. Mandon, C. Billotey, A. Le Meur-Herland, T. Brochard, F. Vocanson, M. Janier, P. Perriat, S. Roux and O. Tillement, J Am Chem Soc, "Gadolinium chelate coated gold nanoparticles as contrast agents for both X-ray computed tomography and magnetic resonance imaging," 2008, 130, 5908-5915.

SUMMARY OF THE INVENTION

An embodiment of the invention is a multicomponent nanomaterial comprising at least one of the following: AuNP(DTDTPA)(Ga) and AuNP(DTDTPA)(biomolecule), where DTDTPA is an amino-carboxylate ligand (diethylene triamine pentaacetic acid, DTPA) linked to the surface of the Au nanoparticle (NP) via dithiol (DT) linkage. Another embodiment is a multicomponent nanomaterial AuNP(DTDTPA)(Ga) with a biomolecule attached, referred to as AuNP(DTDTPA)(Ga)(biomolecule) or AuNP(DTDTPA)(Ga)(B) wherein B stands for a biomolecule. Biomolecules in the present invention are any biomolecules comprising an amine group, including, but not limited to, peptides, antibodies, ScFv antibodies, the Fab portion of an antibody, affibodies, enzymes, proteins and molecules comprising an amine group. In preferred embodiments, the Ga is Ga-67 or Ga-68. Preferred synthesis methods are conducted at room temperature.

Further embodiments include the nanoconstruct AuNP(DTDTPA)(Ga)(B); wherein B is one of the following: a peptide, antibody, affibody, protein or a molecule with at least one amine group available for conjugation.

BRIEF DESCRIPTION OF THE DRAWINGS

FIG. 2 illustrates the synthesis AuNP-(DTDTPA)(Ga) and AuNP-(DTDTPA)(Ga)(B), wherein B is a biomolecule. In FIG. 2A, AuNP-(DTDTPA)(Ga) is first obtained and a biomolecule is then conjugated to the complex to produce AuNP-(DTDTPA)(Ga)(B). In FIG. 2B, AuNP-(DTDTPA) is first conjugated with a biomolecule to produce AuNP-(DTDTPA)(B) and Gallium is then reacted with the complex to produce AuNP-(DTDTPA)(Ga)(B);

DETAILED DESCRIPTION OF THE PREFERRED EMBODIMENTS

Figure 1:
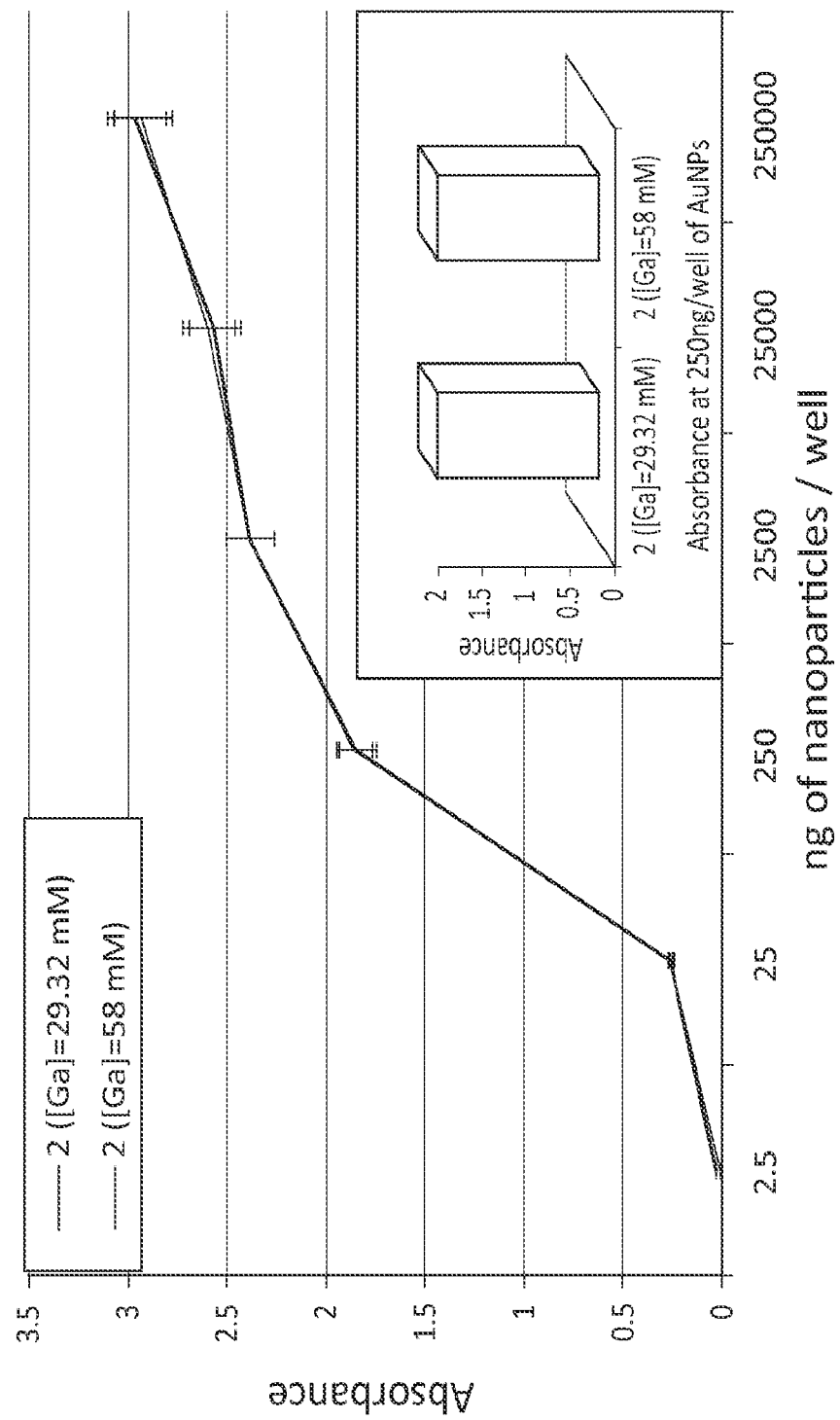
FIG. 1 shows absorbance of conjugated HRP as a biomolecule model with serial 10 fold dilutions of AuNP(DTDTPA)(Ga)

An embodiment of the invention is a multicomponent nanomaterial AuNP(DTDTPA)(Ga) or AuNP(DTDTPA)

(Biomolecule), where DTDTPA is an amino-carboxylate ligand (diethylene triamine pentaacetic acid, DTPA) linked to the surface of the Au nanoparticle (NP) via dithiol (DT) linkage. Another embodiment is a multicomponent nanomaterial AuNP(DTDTPA)(Ga) with a biomolecule attached, AuNP(DTDTPA)(Ga)(B). Biomolecules in the present invention are any biomolecules comprising an amine group available for conjugation, including, but not limited to, peptides, antibodies, ScFv antibodies, the Fab portion of an antibody, affibodies, enzymes, and other proteins and molecules comprising an amine group. All isotopes of Gallium are suitable in these applications. In preferred embodiments, the following isotopes of Gallium can be used: Ga-67 or Ga-68.

Strong attachments are formed. In preferred embodiments, the biomolecule is attached to form a kit. The kit can be shipped to a health facility, and that attachment remains stable. At the health facility, with the room temperature mixing of preferred formation methods, Ga-67 or G-68 can be attached. The solution can then be administered to a patient and imaging can be conducted.

Some embodiments include nanoconstructs AuNP(DTDTPA)(Ga).

Further embodiments include the nanoconstruct AuNP(DTDTPA)(Ga)(B); wherein B is one of the following: a peptide, antibody, affibody or a protein.

The ratios of Au:Ga may be 1:5; 1:2.5 or 1:1.125, and a particular preferred embodiment has the Au:Ga ratio of about 1:5. Preferred solutions of the invention include AuNP(DTDTPA)(Ga) solutions and AuNP(DTDTPA)(Ga)(B) solutions having a concentration in the range of 30 µg/ml to 5 mg/ml with a pH in the range of 6 to 13. In preferred embodiments, Au cores in the multicomponent nanomaterial have a size of ~3-5 nm. Some nanoconstructs have hydrodynamic size of 88 nm and a −55 mV zeta potential.

A preferred synthesis method involves mixing $Ga(NO_3)_3$ (58 mM) with AuNP(DTDTPA) dissolved in NaOH at room temperature with continuous stirring. A preferred AuNP(DTDTPA)(Ga) with a biomolecule synthesis method suspends formed AuNP(DTDTPA)(Ga) in a buffer solution. 1-Ethyl-3-[3-dimethylaminopropyl]carbodiimide hydrochloride (EDC) is added and stirred. Subsequently, a biomolecule in solution is added and continuously stirred and incubated at room temperature for a time period.

Preferred embodiments of the invention will now be discussed with respect to experiments. The experiments illustrate broader aspects of the invention, as will be appreciated by artisans.

In experiments to demonstrate the invention, methods provided synthesis of [AuNP(DTDTPA)(Ga)], characterization of AuNP(DTDTPA)(Ga) using advanced scanning transmission electron microscopy (STEM) techniques; detailed in vitro stability and cytotoxicity studies of AuNP(DTDTPA)(Ga); and synthesis and characterization of [AuNP(DTDTPA)(Ga)(HRP)], as a model for biomolecule attachment. HRP (horseradish peroxidase) has six primary amine residues (lysine), which are available for effective conjugation. (K. G. Welinder, Covalent structure of the glycoprotein horseradish peroxidase (EC 1.11.1.7). 1976, FEBS Lett. 72, 19-23). In general, biomolecule conjugation can be achieved if biomolecules contain free amino groups. Antibodies, affibody, and proteins have free amino groups that attach with the nanoparticle in a similar fashion. Peptides not containing aminogroups on the other hand, can be attached to AuNP-DTDTPA using thiol groups incorporated within the peptides. Thiol groups attach with gold nanoparticles on the surface.

The experiments showed that layered carboxylate structure plays an important role for attachment. The experiments confirmed that the multilayered carboxylate architecture is fairly stable over a wide range of pH (6 to 13) and at different concentrations (30 µg/ml to 5 mg/ml).

[AuNP(DTDTPA)(Ga)] was synthesized by treating AuNP(DTDTPA) conjugate with $Ga(NO_3)_3$ at pH 8.0. The optimized ratio determined Au:Ga is 1:5. Complex AuNP(DTDTPA)(Ga) exhibits a core size of ~3-5 nm, hydrodynamic size of 88 nm and a −55 mV zeta potential. Serial titrations determined the maximum concentration of gallium that can be incorporated within the nanoconstruct (AuNP(DTDTPA) conjugate). Specifically, serial titrations of AuNP(DTDTPA) conjugate with $Ga^{3+}$ were performed and evaluated the resultant conjugate using both Ga-71 NMR spectroscopy and ICP-OES analysis. The NMR active $^{71}Ga$ is used as a probe to determine the concentration of chelated Ga. NMR of different concentrations of $Ga(NO_3)_3$ were recorded in $D_2O$. A standard curve using concentrations of non-chelated Ga vs. peak integration values were plotted. Using the plot, it was determined that 11 mM of Au can irreversibly chelate up to 58 mM of Ga. These results indicate any gallium added beyond this concentration would not be chelated with AuNP-DTDTPA.

The NMR results were validated by performing additional experiments using ICP-OES. In this experiment, the Au/Ga ratios of the resultant conjugates were monitored after treatment of 11 mM of AuNP(DTDTPA) conjugate (Au) with different amounts of $Ga^{3+}$. The Au/Ga ratio becomes a constant after addition of 58 mM of $Ga^{3+}$. These experiments establish the exact concentration of Ga that can be irreversibly chelated to AuNP(DTDTPA) conjugate. The smaller core size of AuNP(DTDTPA)(Ga) made the characterization quite challenging.

Multiple analytical tools (UV-Vis, TEM, DLS, XPS, EDX, HAADF, and EELS) were used to obtain structural details of AuNP(DTDTPA)(Ga). Conventional techniques such as UV-Vis and TEM confirmed that the crystallinity of gold core AuNP(DTDTPA) conjugate is retained after chelation with Ga. As the gold core size is less than 5 nm, the surface plasmon resonance showed a small hump at 520 nm before and after complexation.

$Ga^{3+}$ may effectively complex with carboxylate anions and amines closer to the surface of gold. AuNP-DTDTPA-Ga structure was further analyzed by using XPS measurements. Of particular interest is the binding of gallium to the surface ligand, DTDTPA. Surface bound DTDTPA is rich in disulfides, secondary amines, and carboxylates. Even though the metallic alloy of Ga with Au is known at 400° C., it is unexpected in the present scenario, and the invention provides a surprising result with room temperature formation. The room temperature formation is advantageous to maintain desirable properties. Also the ability to attach a biomolecule at room temperature is advantageous to avoid harm to the biomolecule.

It is possible that $Ga^{3+}$ can bind with thiol; however, thiols are present predominantly as disulfides in the parent nanoconstruct. Such a binding would require oxidative addition of $Ga^{3+}$ across disulfide bonds, which is not feasible based on the chemistry of gallium. However, N and O atoms present in the ligand is geometrically positioned to chelate with Ga. In the conjugate AuNP(DTDTPA)(Ga), the N(1S) levels showed a peak at 398.8 eV.

Having established the synthesis and characterization of [AuNP(DTDTPA)Ga] (2) conjugate, the inventors focused our attention to explore further utilization of carboxylate ligands on AuNP(DTDTPA)(Ga) for conjugating with biomolecules. For proving the concept that such conjugation was feasible, the inventors used HRP (horseradish peroxidase) as a biomolecule. The inventors conjugated HRP to AuNP(DTDTPA)(Ga) to demonstrate this biomolecule was successfully conjugated to AuNP(DTDTPA)(Ga). Presence of HRP was detected by conventional ELISA technique. The inventors utilized two different conjugates of AuNP(DTDTPA)(Ga), with varying amounts of Ga present in each of the two nanoconjugate samples; namely, conjugate samples obtained after treatment of AuNP(DTDTPA) conjugate with 29 mM of Ga, and other samples with the saturating amount of 58 mM. Low concentration of gallium (less than required for complete chelation) was used deliberately to increase the number of free carboxylates, while a very high amount (more than required for complete chelation) was used to utilize all possible carboxylates present in the nanoconstruct. The absorbance of conjugated HRP was plotted against concentration of nanoconstruct (AuNP(DTDTPA)(Ga)) to relate the binding capabilities.

FIG. 1 shows absorbance of conjugated HRP with serial 10 fold dilutions of AuNP(DTDTPA)(Ga). The absorbance increases with increasing concentration of AuNP(DTDTPA)(Ga) as the HRP holding capability of AuNP(DTDTPA)(Ga) increases. On the other hand, chelates with varying concentrations of Ga (29 mM and 58 mM) did not show any difference in conjugation with HRP (inset). These data shows that HRP conjugation with AuNP(DTDTPA)(Ga) is independent of amount of chelated Ga.

The data can be interpreted to show that HRP is conjugated with sterically less-crowded carboxylates that are available after gallium chelation on the nanoparticle. While not necessary to practice the invention and without being bound to the theory, a theory supported by the data is that the carboxylates located on the surface attached DTDTPA ligand exhibit two orientational types of carboxylates; namely, those that form a compact carboxylate structure that takes part in chelation with Ga, and a second orientational type of carboxylate that are not conformationally favorable to form a thermodynamically stable metal chelate. The second kind of carboxylates is available for biomolecule conjugation. The possibility of interaction of gallium atoms with the conformationally unfavorable carboxylates is minimal. Due to this binding preference of gallium and HRP, the HRP conjugation efficiency remains the same for both low (29 mM) and high (58 mM) gallium chelated AuNP.

The cytotoxicity of AuNP(DTDTPA) conjugate and AuNP(DTDTPA)(Ga) was studied on human prostate cancer (PC-3) cells under in vitro conditions using a colorimetric cell-viability (MTT) assay. The results demonstrate that nanoconstructs AuNP(DTDTPA) conjugate and AuNP(DTDTPA)(Ga) do not show cytotoxicity up to 40 µg/mL concentrations. Nevertheless, the cell viability was slightly lesser for AuNP(DTDTPA)(Ga) than AuNP(DTDTPA) conjugate for the period of 24 h post treatment. The AuNP are themselves non-toxic. In addition, the experiments showed that nanoconstruct AuNP(DTDTPA) conjugate, containing DTDTPA ligand coating on the surface of AuNPs, is also non-toxic. Therefore, the minimal toxicity exhibited by AuNP(DTDTPA)(Ga) may be attributed to conjugated gallium. The lack of any noticeable toxicity of AuNP(DTDTPA) conjugate and AuNP(DTDTPA)(Ga) make these nanomaterials suitable for biomedical imaging.

Experimental Materials

The materials used for synthesis of gold nanoparticle (AuNPs) were procured commercially. Tetrachloroauric acid trihydrate ($HAuCl_4 \cdot 3H_2O$), sodium borohydride ($NaBH_4$), diethylenetriaminepentacetic acid (DTPA), acetic anhydride, anhydrous pyridine, 2-aminoethanethiol hydrochloride, triethylamine, glacial acetic acid ($CH_3COOH$), Gallium nitrate ($Ga(NO_3)_3$), sodium hydroxide (NaOH), hydrocloric acid (HCl), methanol (MeOH), diethyl ether ($Et_2O$), sodium chloride (NaCl), dimethyl formamide (DMF), dimethyl sulfoxide (DMSO), histidine, human serum albumin (HSA), bovine serum albumin (BSA), and cysteine were purchased from Aldrich Chemical, USA and used as received. For the preparation of aqueous solutions and for rinsing of gold nanoparticles, Milli-Q (DI) water ($\rho > 18$ MΩ) was used. Synthesis of AuNP(DTDTPA) conjugate was performed by previously reported protocol. See, C. Alric, J. Taleb, G. Le Duc, C. Mandon, C. Billotey, A. Le Meur-Herland, T. Brochard, F. Vocanson, M. Janier, P. Perriat, S. Roux and O. Tillement, J Am Chem Soc, "Gadolinium chelate coated gold nanoparticles as contrast agents for both X-ray computed tomography and magnetic resonance imaging," 2008, 130, 5908-5915. MTT Cell Proliferation Assay kit was obtained from Promega Corporation, USA.

Synthesis of AuNP-(DTDTPA)(Ga)

Aqueous solution of $Ga(NO_3)_3$ (58 mM) was mixed with AuNP(DTDTPA) conjugate (11.36 mM of [Au]) dissolved in 0.01M NaOH at room temperature with continuous stirring. Immediate precipitate formation was observed. The reaction mixture was allowed to stir for 3 hours and subsequently washed with DI water (three times) and centrifuged at 20000 rcf for 20 mins at 25° C. rcf is relative centrifugal force, and corresponds to the force associated with 1 g, where g is the acceleration of gravity at the surface of the Earth. FIG. 2 illustrates the synthesis AuNP-(DTDTPA)(Ga), AuNP-PEG+Ga, TA-AuNP+Ga with respective HR-TEM and EDX Spectra confirming the presence and absence of Ga cations. As shown in FIG. 2A, AuNP-(DTDTPA)(Ga) may be first obtained and a biomolecule is then conjugated to the complex to produce AuNP-(DTDTPA)(Ga)(B). Alternatively and as shown in FIG. 2B, AuNP-(DTDTPA) may first be conjugated with a biomolecule to produce AuNP-(DTDTPA)(B) and Gallium is then reacted with the complex to produce AuNP-(DTDTPA)(Ga)(B).

Analysis of AuNP-(DTDTPA)(Ga)

To a solution of AuNP(DTDTPA) conjugate (11.36 mM of [Au]) dissolved in 0.01M NaOH, a solution of increasing amounts of $Ga(NO_3)_3$ (3.9, 9.7, 19.5, 39, 58, 78, 117, 156 mM) in DI water was added. The chelated product was isolated. 1 mg/ml of the dried pellet (dissolved in 0.01M NaOH) and respective supernatants were used for ICP analysis. All measurements were performed in triplicates. To evaluate concentration of Ga that are irreversibly chelated to AuNP(DTDTPA) conjugate, the inventors determined the concentrations of [Ga] and [Au] in AuNP-(DTDTPA)(Ga). Based on ICP-OES analysis, it was evident that Au/Ga ratio remains constant beyond 58 mM concentration of [Ga].

$^{71}$Ga NMR Spectroscopy

Figure 3:
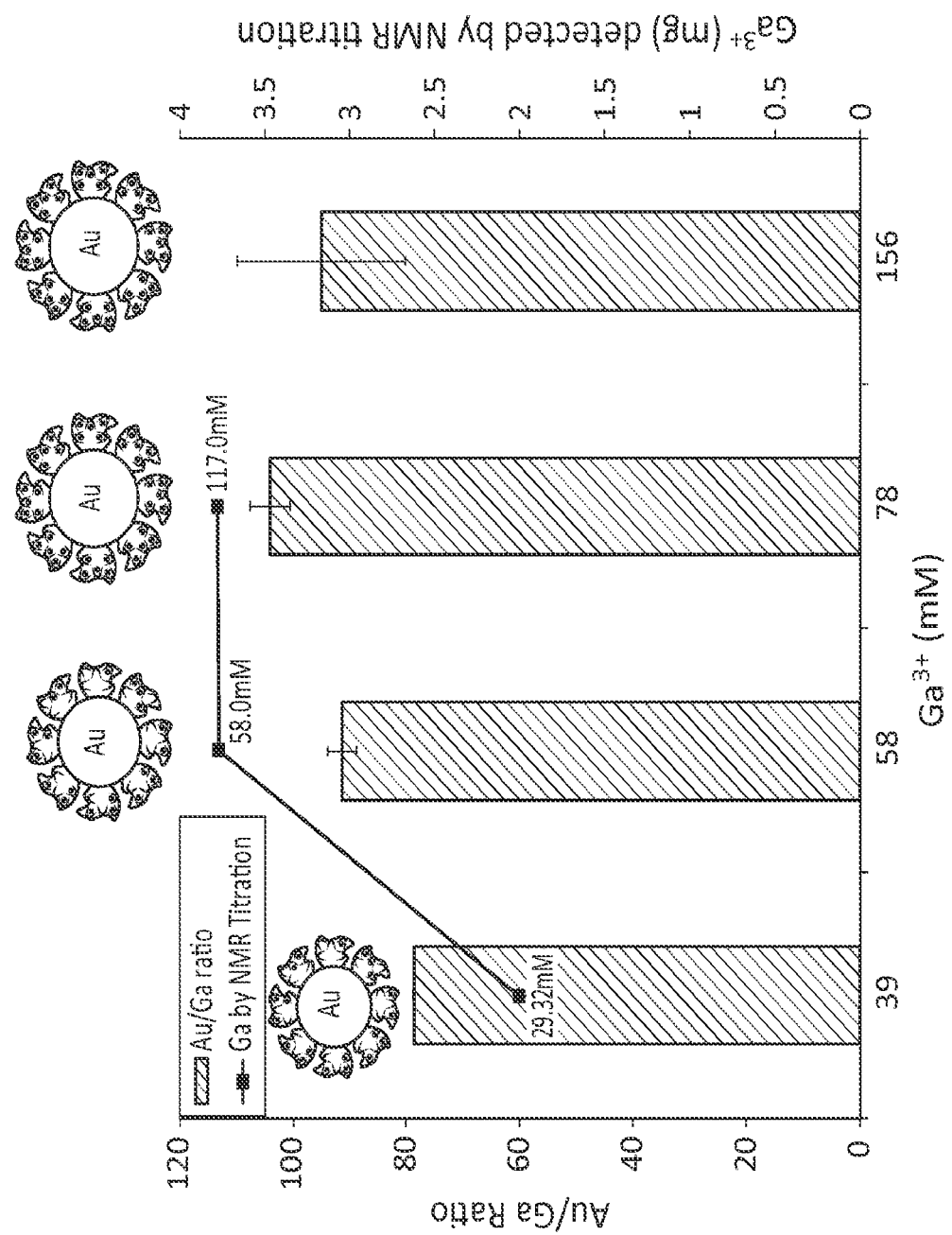
FIG. 3 shows data concerning titration of $Ga(NO_3)_3$ with AuNP(DTDTPA) conjugate and the amount of $Ga^{3+}$ detected by ICP-OES and $^{71}$Ga-NMR in terms of Au/Ga ratio and $Ga^{3+}$ in mg, respectively.
Figure 4:
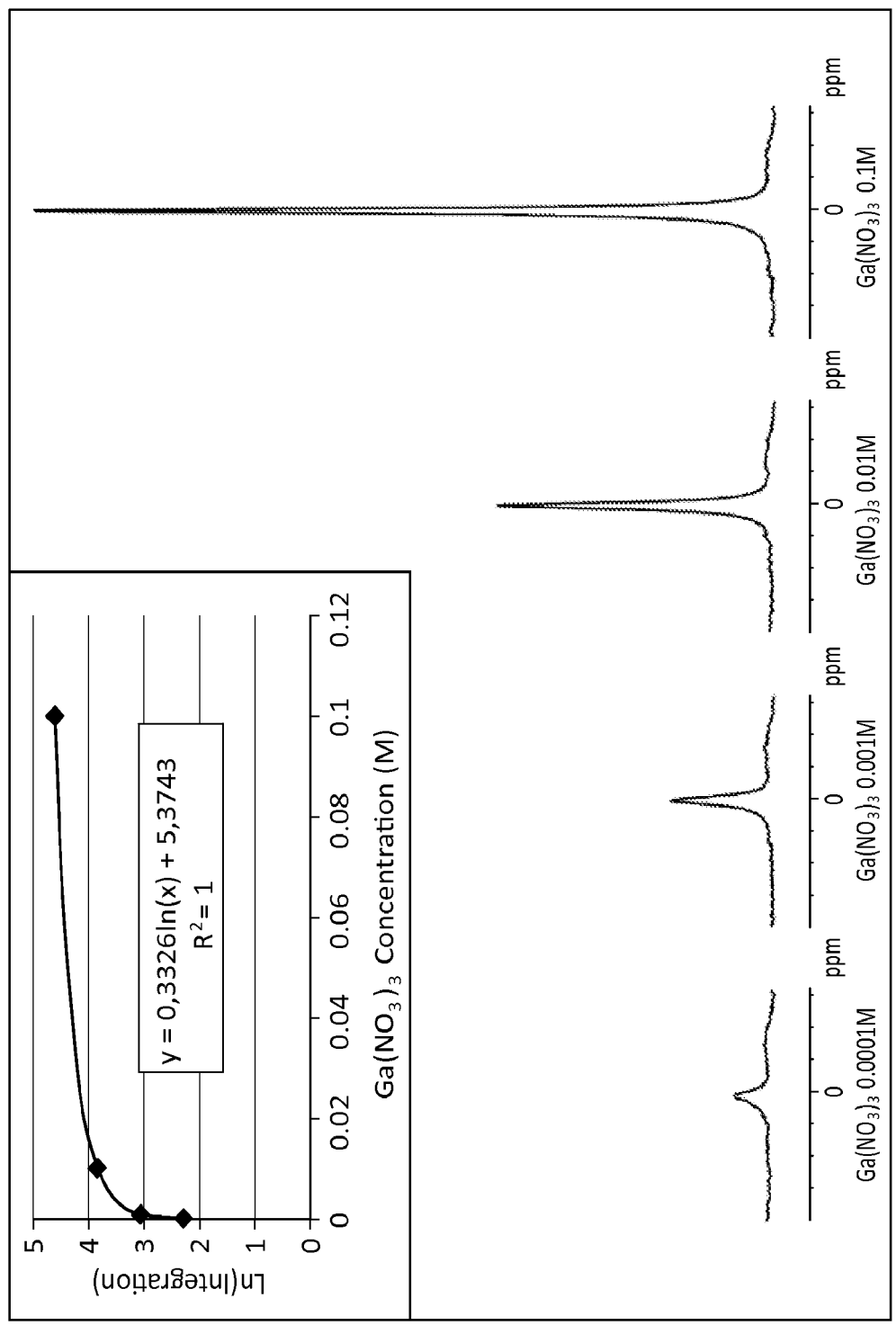
FIG. 4 shows $^{71}$Ga NMR spectra of the standard solutions of $Ga(NO_3)_3$ with concentrations of 0.1M, 0.01M, 0.001M, and 0.0001M in $D_2O$.
Figure 5:
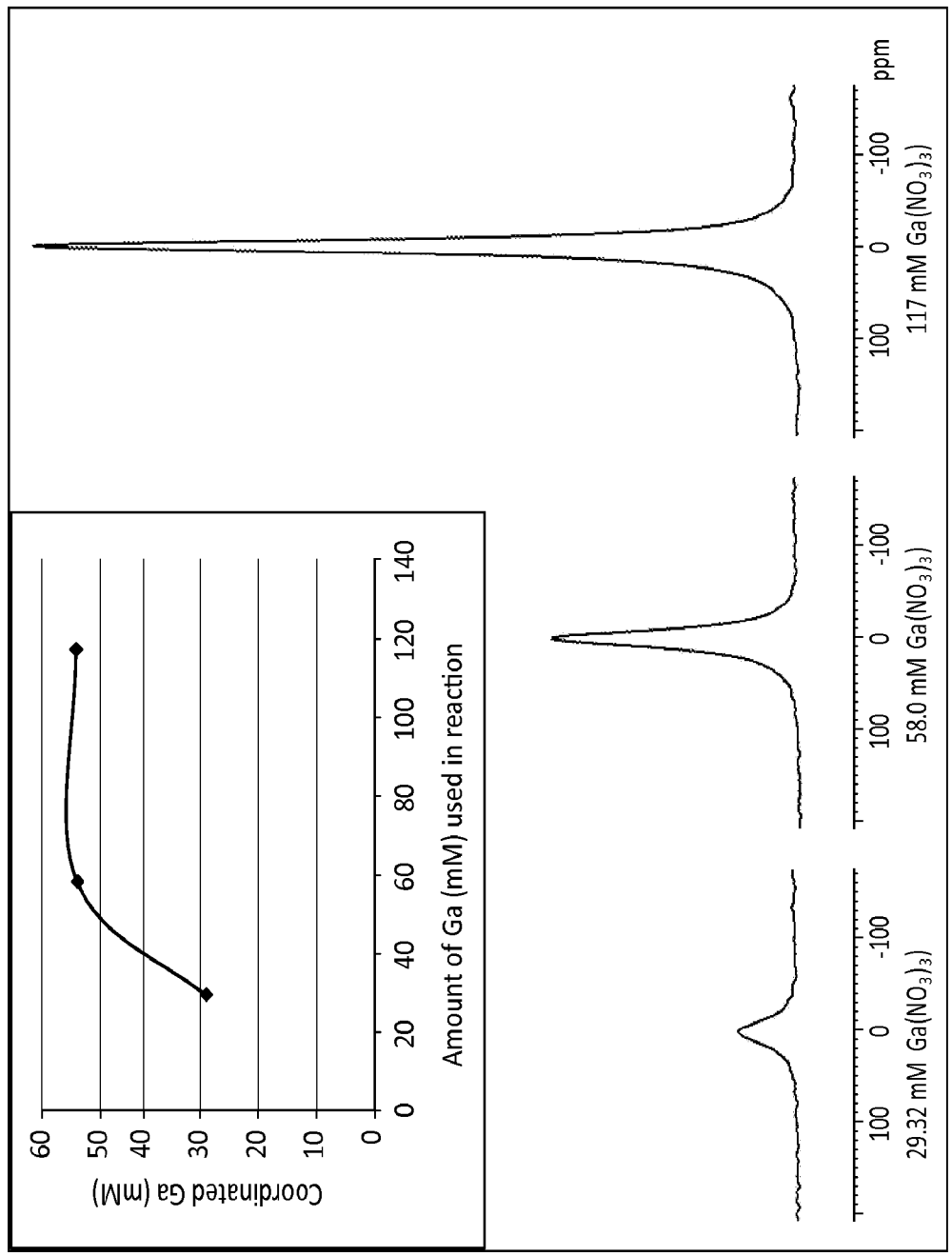
FIG. 5 shows $^{71}$Ga NMR spectra of the reaction supernatants of 1 with different amounts of $Ga(NO_3)_3$.

FIG. 3 shows titration of $Ga(NO_3)_3$ with AuNP(DTDTPA) conjugate and the amount of $Ga^{3+}$ detected by ICP-OES and $^{71}$Ga-NMR in terms of Au/Ga ratio and $Ga^{3+}$ in mg, respectively. For titration using $^{71}$Ga NMR spectroscopy, four different standard solutions of $Ga(NO_3)_3$ with the respective concentrations, 0.1M, 0.01M, 0.001M and 0.0001M, were prepared in $D_2O$. $^{71}$Ga NMR was recorded for each of these standard solutions and peak integration values were noted. It is well-known that $^{71}$Ga NMR strongly depends on the symmetry of the complex. If the gallium containing complex lacks symmetry, the NMR signal disappears. Various concentrations of $Ga(NO_3)_3$ (29.3 mM; 58.6 mM or 117 mM) were added to aqueous solutions of AuNP(DTDTPA) conjugate (5 mg/mL). After stirring for 3 hours, the reaction mixtures were centrifuged (20,000 rcf, 20 min, 25° C.) and the supernatants decanted and concentrated to 1 mL volume. Supernatant solutions were analyzed and peak integration values were used to calculate the amount of gallium present [Peak integration and concentrations of [Ga] were standardized by a separate experiment (see FIG. 3). The slope of the straight line in the graph was a best fit to the data, and corresponded to the amount of gallium that can be coordinated to AuNP(DTDTPA) conjugate (5 mg). By this NMR experiment, it is clear that 11.36 mM of [Au] in AuNP(DTDTPA) conjugate requires at least 58 mM of [Ga]. FIG. 4 shows $^{71}$Ga NMR spectra of the standard solutions of Ga(NO$_3$)$_3$ with concentrations of 0.1M, 0.01M, 0.001M, and 0.0001M in D$_2$O. Through the integration of the $^{71}$Ga NMR peaks a standard curve of the logarithmic integration was obtained for the different known solutions of Ga(NO$_3$)$_3$ as shown in inset. It should be noted that the integrations were done considering the integration value of 100 to be associated with the highest concentrated solution of Ga(NO$_3$)$_3$ (0.1M). FIG. 5 shows $^{71}$Ga NMR spectra of the reaction supernatants of 1 with different amounts of Ga(NO$_3$)$_3$. The inset shows the amount of gallium coordinated to 11.36 mM [Au] in AuNP-DTDTPA at various concentrations of Ga(NO$_3$)$_3$.

Synthesis of Conjugates of AuNP-(DTDTPA)(Ga)

Two different conjugates of AuNP-(DTDTPA)(Ga) differing in gallium ion concentrations were synthesized. The gallium chelated gold nanoparticles, AuNP-(DTDTPA)(Ga) ([Au]=11.36 mM and [Ga]=29.32 mM and 58.0 mM), were suspended in 1×PBS. To 500 μl of AuNP-(DTDTPA)(Ga), 28 μg of I-Ethyl-3-[3-dimethylaminopropyl]carbodiimide hydrochloride (EDC) was added in 0.1M 2-(N-morpholino) ethane sulfonic acid (MES) buffer (pH 4.6). The reaction was stirred for 10 min at room temperature. After 10 minutes, HRP solution (0.454M) was added to the reaction mixture in 200 μl of 0.1M MES buffer (pH 4.6) and incubated for 4 hours at room temperature with continuous stirring. Reaction mixture was centrifuged at 13500 rcf for 10 minutes at 25° C. and the pellet was subsequently washed twice with 1×PBS and suspended in 1×PBS solution. Both the pellets and supernatants were used for peroxidase activity assay. The serial increase in absorption of nanoparticles (AuNP-(DTDTPA)(Ga))-HRP conjugate was monitored and correlated to the binding of HRP protein to AuNP-(DTDTPA)(Ga). The outer layer carboxylates in AuNP-(DTDTPA)(Ga) were activated using EDC in an activation buffer and conjugated with HRP. The conjugate was characterized by peroxidase assay using ELISA and also by measuring zeta potential, size, TEM and TEM with EDX. The EDX spectrum from a group of nanoparticles showed the presence of gold and gallium in HRP conjugated nanoconstruct on a copper/carbon grid.

Peroxidase Activity Assay Using ELISA

In a 96-well plate, 100 μl of 3 was added in the first row and serial 10 fold dilutions of the samples were made along each column using 1×PBS. To all the wells was added 50 μL of TMB (3,3',5,5'-Tetra Methyl Benzidine) and one component of substrate was added. The plate was incubated at room temperature for 5 minutes and further the activity of the enzyme was stopped by addition of 50 μL of 1M HCl. The absorbance of the individual wells was recorded on a microplate reader at 450 nm immediately. The ELISA studies were representative measurements from triplicates, and the readings were plotted as a graph of mass (in units of ng) of particles versus absorbance. HRP was used traditionally as a labeling agent for C-terminal of various proteins, and presence of HRP was analyzed via coupled enzyme assays.

In Vitro Stability

Figure 6B:
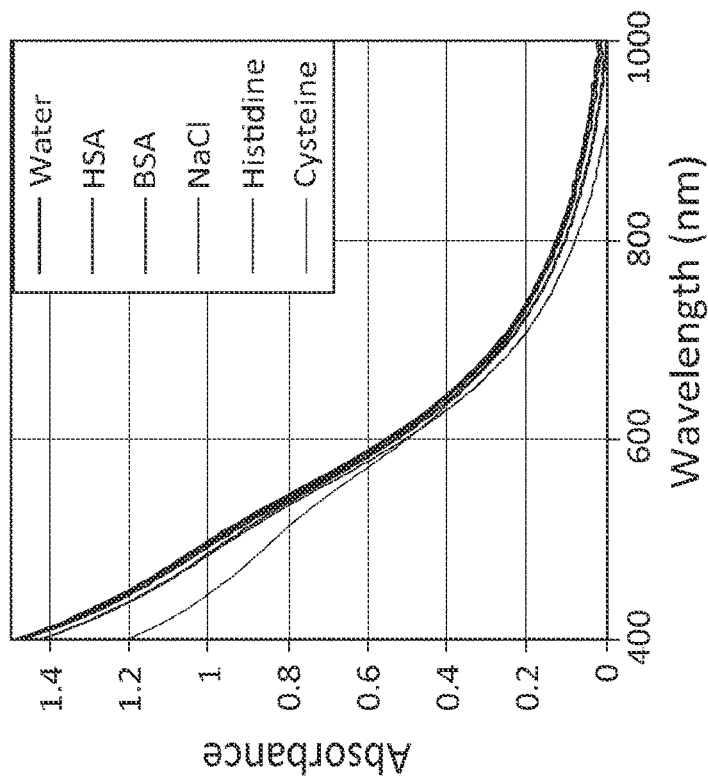
FIG. 6A and FIG. 6B respectively illustrate data from in vitro stability studies of AuNP(DTDTPA) conjugate and AuNP-(DTDTPA)(Ga) under various biological media.
Figure 6A:
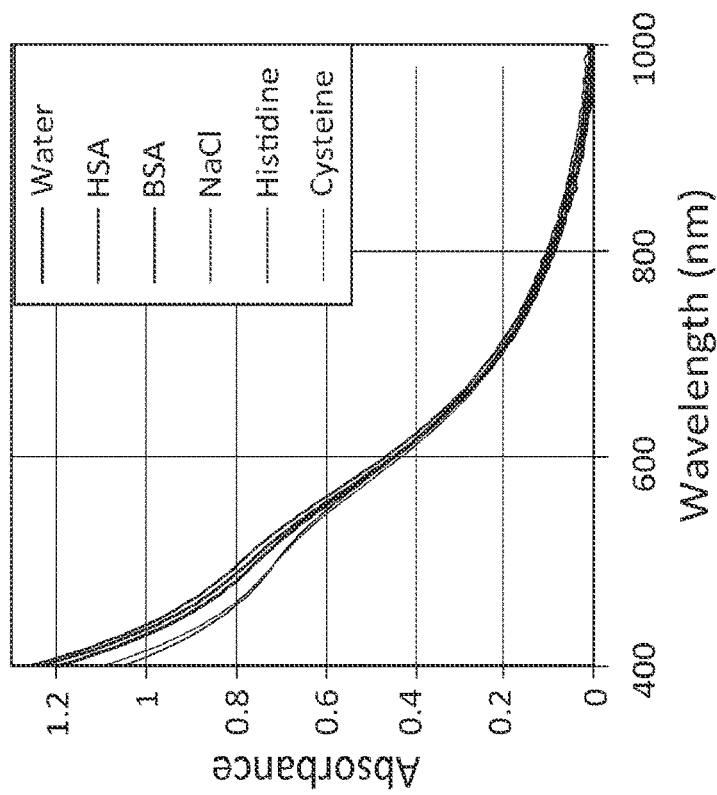

In vitro stability studies were performed by incubating solutions of AuNP(DTDTPA) conjugate and AuNP-(DTDTPA)(Ga) at various pH conditions: 2, 5, 7, 10 and 12 for the period of 24 hours. The stability behavior for both were also monitored by challenging aqueous solutions of AuNP (DTDTPA) conjugate and AuNP-(DTDTPA)(Ga) (0.5 mL) with 0.5 mL each of 0.2M cysteine, 0.2M histidine, 0.2M HSA and 10% saline solutions. The stability was measured by monitoring the UV-visible absorbance, hydrodynamic radius and zeta potential measurements at 0 hour to 96 hours (namely, at 0, 1, 24, 48, 72, and 96 hours). A negligible change in UV-Vis plasmon band of AuNP(DTDTPA) conjugate and AuNP-(DTDTPA)(Ga) confirmed the retention of nanoparticulate composition with stable behavior in all the challenging solutions except cysteine. The treated solutions did not show any noticeable change in hydrodynamic radii, thus confirming the stability of these conjugates. FIG. 6A and FIG. 6B, respectively, illustrate data from in vitro stability studies of AuNP(DTDTPA) conjugate and AuNP-(DTDTPA)(Ga) under various biological media of 10% NaCl, 0.5% cysteine, 0.2M histidine, 0.5% HSA, and 0.5% BSA solutions. UV-visible absorption spectra of these solutions after 24 hours treatment were recorded.

Characterization of AuNP(DTDTPA) Conjugate

The core size of AuNP(DTDTPA) conjugate that showed the hydrodynamic diameter of 88 nm as observed by DLS measurements was 2-3 nm as observed from TEM images. This result validates the preservation of multilayered structure of DTDTPA on AuNP surface. Any disturbance to H-bonding network would result in destabilization of DTDTPA structural motif and these disturbances would arise from pH variations and dilutions. The changes in hydrodynamic diameter and zeta potential due to pH and dilutions have been monitored by DLS measurements.

Effect of pH

The experiment was performed on the pH range from 2-13. A strong dependence of size with pH variation was observed. This dependence is shown in Table 1. At lower pH (pH 2) the size was 2417 nm. This hydrodynamic size increase is attributed to the protonation of —COOH groups at low pH resulting in aggregation of nanoparticles. At pH 4, a decrease in size to ~213 nm was observed due to decreased protonation. However, within a pH range of 6-13, the hydrodynamic diameters of AuNP(DTDTPA) conjugate remained constant at 78±4 nm, thus ensuring that the layered structure is intact and stable in this pH range.

TABLE 1

Size analysis and zeta potential measurements of 1 at standard pH buffer solutions

| Conc. of 1 (mg/ml) | pH | Conc of Au (mM) | Size by DLS (nm) Mean | Std dev | Zeta Potential (mV) Mean | Std dev | Observations |
|---|---|---|---|---|---|---|---|
| 0.50 | 2 | 1.16 | 2417 | 315 | 19 | 1.06 | Suspension |
| 0.50 | 4 | 1.16 | 213 | 1.60 | −32 | 1.41 | Partially Soluble |
| 0.50 | 5 | 1.16 | 212 | 1.60 | −40 | 0.28 | Partially Soluble |
| 0.50 | 6 | 1.16 | 76 | 0.39 | −33 | 2.90 | Soluble (Clear Solution) |

TABLE 1-continued

Size analysis and zeta potential measurements of 1 at standard pH buffer solutions

| Conc. of 1 (mg/ml) | pH | Conc of Au (mM) | Size by DLS (nm) Mean | Std dev | Zeta Potential (mV) Mean | Std dev | Observations |
|---|---|---|---|---|---|---|---|
| 0.50 | 9 | 1.16 | 82 | 1.00 | −54 | 0.14 | Soluble (Clear Solution) |
| 0.50 | 11 | 1.16 | 78 | 1.17 | −53 | 0.98 | Soluble (Clear Solution) |
| 0.50 | 13 | 1.16 | 74 | 0.62 | −48 | 2.60 | Soluble (Clear Solution) |

Effect of Dilution

The inventors also studied the effect of dilution on the layered structure of AuNP(DTDTPA) conjugate using DLS. The data are shown in Table 2. With increased concentration of AuNP(DTDTPA) conjugate, from 0.3 mg/mL (Au=0.05 mM) to 5 mg/mL (Au=11.36 mM) in DI water at pH 8-8.5, no change in hydrodynamic size (average particle size=88±4 nm) or zeta potential (average zeta potential=−72 mV) was observed.

TABLE 2

Size analysis and Zeta potential measurements of 1 at various dilutions

| Conc. of 1 (mg/ml) | Dilution | Conc of Au (mM) | pH | Size by DLS (nm) Mean | Std dev | Zeta Potential (mV) Mean | Std dev | Size by NTA (nm) |
|---|---|---|---|---|---|---|---|---|
| 0.03 | 5 ul of stock | 0.050 | 7.80 | 92 | 2.14 | −70 | 0.78 | ND |
| 0.05 | 10 ul of stock | 0.101 | 8.18 | 88 | 0.16 | −80 | 0.49 | ND |
| 0.13 | 25 ul of stock | 0.303 | 7.92 | 90 | 1.05 | −77 | 0.21 | 77 |
| 0.25 | 50 ul of stock | 0.555 | 7.91 | 90 | 0.85 | −79 | 4.73 | 98 |
| 0.50 | 100 ul of stock | 1.16 | 8.53 | 88 | 0.65 | −71 | 0.21 | 63 |
| 1.00 | 200 ul of stock | 2.27 | 8.73 | 84 | 0.3 | −68 | 0.49 | 102 |
| 1.00 | 200 ul of stock - recorded after 24 h | 2.27 | 8.73 | 84 | 0.42 | −65 | 2.96 | ND |
| 5.00 | Stock Solution | 11.36 | — | 126 | 2.08 | NM | — | NM |

ND: Not Determined;
NM: Not Measurable

Characterization of AuNP-(DTDTPA)(Ga)

To understand the effect of Ga chelation on the layered structure, the inventors performed a detailed DLS study using the Ga chelated conjugate AuNP-(DTDTPA)(Ga) at pH 8. If some of the carboxylate anions in AuNP(DTDTPA) conjugate will complex with $Ga^{3+}$ ions, the resultant negative charge will be relatively less than the parent construct. The zeta potential of AuNP-(DTDTPA)(Ga) is −55 mV (−81 mV for AuNP(DTDTPA) conjugate) and the difference is ~25 mV, suggesting the presence of free carboxylic groups and also confirming the layered structure even after chelation. The TEM images of AuNP-(DTDTPA)(Ga) also clearly indicated that the nanoparticles are arranged in a cluster of several nanoparticles. It is expected that a cluster of 50-60 nanoparticles interact through macromolecular H-bonding. Such H-bonding network between nanoparticulate structures is not unusual. Further, as Ga ions surround AuNP, another layer of carboxylate is available to form conjugation with biomolecule. This experiment confirmed that the structural integrity of multilayer carboxylates present in the parent AuNP(DTDTPA) conjugate is retained.

Nanoparticle Tracking Analysis (NTA)

Nanoparticle tracking analysis (NTA) was also performed on both AuNP(DTDTPA) conjugate and AuNP-(DTDTPA)(Ga) to confirm the structural integrity by tracking nanoparticles simultaneously moving under Brownian motion using NTA. The average particle size by NTA confirmed hydrodynamic diameter of ~85 nm for AuNP(DTDTPA) conjugate and no major change in size was observed for conjugate AuNP-(DTDTPA)(Ga) (~98 nm) confirming that the structural integrity is preserved upon chelation.

Investigation of $Ga^{3+}$ Binding on AuNPs

Systematic experiments have been performed to confirm the chelation of gallium atoms with DTDTPA and not present on the surface of AuNPs. To understand whether the gold nanoparticle surface has affinity towards $Ga^{3+}$ ions, two different "model" gold nanoparticles were chosen.

The first model AuNP that the inventors chose was AuNP coated with thiolated PEG-750 (AuNP-PEG-750), wherein, the charge (zeta potential) of AuNP ($\zeta$=−49 mV) is similar to that of AuNP(DTDTPA) ($\zeta$=−81 mV) but does not contain any chelating ligand such as DTDTPA on the surface. AuNP-PEG-750 (characterized independently) was treated with different ratios of $Ga^{3+}$. The reactions were performed under identical conditions, as were utilized and followed for the preparation of AuNP-(DTDTPA)(Ga). The nanoconstructs obtained were characterized by HR-TEM, EDX, UV-Visible, size and zeta analysis and the data were compared with AuNP-(DTDTPA)(Ga).

The second model was AuNP coated with thioctic acid (AuNP-TA). The rationale for choosing (AuNP-TA) is as follows: (a) TA group has carboxylates outside; however, it lacks chelating ligand structures as present in DTPA. (b) TA also has size (core size 3-5 nm), which is a size similar to that of AuNP(DTDTPA) (1). (c) Additionally the synthetic route for preparation of TA-AuNP is also similar to those of AuNP(DTDTPA). The reaction of $Ga^{3+}$ with TA-AuNP was performed under identical conditions as followed for the preparation of AuNP-(DTDTPA)(Ga). Final product was thoroughly characterized by HR-TEM, EDX, UV-Visible, size and zeta analysis and data were compared with those of AuNP-(DTDTPA)(Ga).

Reaction of AuNP-PEG with $Ga(NO_3)_3$-(AuNP-PEG+Ga): $Ga(NO_3)_3$ dissolved in water was added to AuNP-PEG (10.05 µM [Au]) in different molar ratios (Au:Ga ratio; 1:5, 1:2.5, 1:1.125) and stirred for 3 hours at room temperature. Gold mirror formation was observed on the walls (ES-FIG.

17) within 5 minutes of gallium nitrate addition at all ratios. The solution was centrifuged (20,000 rcf for 20 min) after 3 hours and pellets obtained were washed three times, resuspended in DI water and used for characterization.

Reaction of TA-AuNP with Ga(NO$_3$)$_3$-(TA-AuNP+Ga): Ga(NO$_3$)$_3$ dissolved in water was added to TA-AuNP (6.7 μM [Au]) in 1:5 (Au:Ga) molar ratio and after 30 minutes of addition, precipitate formation was observed and stirring was continued for 3 additional hours at room temperature. The solution was centrifuged (20,000 rcf for 20 min) to obtain pellet and subsequently washed three times with DI water. The pellet obtained was resuspended in 0.01M NaOH and used for characterization.

HR-TEM images obtained for AuNP-PEG+Ga pellet (Au:Ga, 1:5) were not significantly different from those of AuNP-PEG except that larger size nanoparticles were observed. The formation of larger size nanoparticles resulted due to the aggregation induced by addition of Ga(NO$_3$)$_3$. With respect to TA-AuNP+Ga reaction, the final pellet did not show any change in size and distribution of the particles.

The EDX spectra of pellets obtained by addition of gallium nitrate to (AuNP-PEG (Au:Ga; 1:5) and (TA-AuNP (Au:Ga; 1:5) were recorded. Point and shoot technique was used to scan individual nanoparticles and the surrounding area. Scanning was performed additionally throughout the grid including dense nanoparticle regions. If any gallium were to be adhered to the surface of gold nanoparticle, then gallium signals would appear correspondingly. The absence of Ga kα signal at 9.25 in pellets (AuNP-PEG+Ga (1:5)) and (TA-AuNP+Ga (1:5)), clearly indicating that there is no affinity between gold nanoparticles and gallium ions.

The experimental results presented unambiguously validate that Ga ions do not attach on the surface of gold nanoparticles. STEM-HAADF image data and HR-TEM-EDX analysis of AuNP-(DTDTPA)(Ga) indicated that at point O$_2$, which is located in between gold cores (away from the gold surface), we detect the presence of Ga as well as a high carbon and oxygen content. This result is an independent proof that Ga$^{3+}$ is chelated by DTDTPA, while conventional belief is that direct interactions of Au and Ga are feasible only at high temperature (300-400° C.). Our analytical data for AuNP-(DTDTPA)(Ga) and results from "model" nanoparticles confirm that Ga ions are not bound on the surface of gold nanoparticles.

Figure 7:
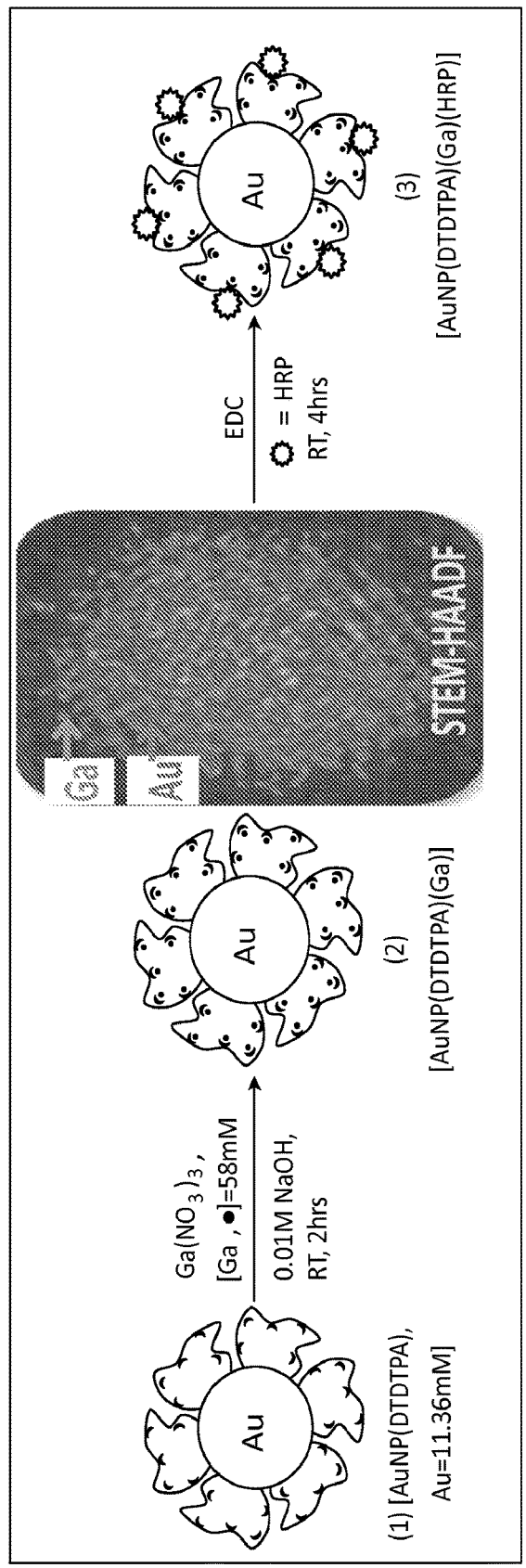
FIG. 7 illustrates a preferred room temperature process for conjugation of AuNP-(DTDTPA)(Ga) and AuNP-(DTDTPA)(Ga)HRP.

FIG. 7 summarizes preferred synthesis. In phase 1 to phase 2, the AuNP-(DTDTPA)(Ga) is formed at room temperature. HRP is attached as a biomolecule model.

Example 1

By determination of the amount of Au by AAS and the amount of Ga by ICP-OES, the inventors have calculated that the maximum molar ratio Ga:Au that can be obtained is ≈1.2, which means that there is slightly more Ga in the AuNPs than Au. This is actually a plausible result if one takes into account that the Au cores are very small (3-5 nm) and the polymeric coating of DTDTPAs can coordinate considerable amount of Ga. The zeta potential value of 2 (−81 mV (1) to −55 mV) shows a positive shift indicating coordination of electropositive gallium coordination.

In order to investigate the maximum concentration of gallium that can be incorporated within the nanoconstruct (1) the inventors performed serial titrations of 1 with Ga$^{3+}$ and evaluated the resultant conjugate using both Ga-71 NMR spectroscopy and ICP-OES analysis (See FIG. 3). The NMR active 71Ga is used as a probe to determine the concentration of chelated Ga. NMR of different concentrations of Ga(NO$_3$)$_3$ were recorded in D2O (See Table 3). A standard curve using concentrations of non-chelated Ga vs. peak integration values were plotted. Using the plot, the inventors determined that 11 mM of Au can irreversibly chelate up to 58 mM of Ga. That indicates any gallium added beyond this concentration would not be chelated with AuNP-DTDTPA. The NMR results were validated by performing additional experiments using ICP-OES. In this experiment, the inventors monitored Au/Ga ratios of the resultant conjugates after treatment of 11 mM of 1 (Au) with different amounts of Ga$^{3+}$. Au/Ga ratio becomes a constant after addition of 58 mM of Ga$^{3+}$. By these experiments, the inventors have demonstrated the exact concentration of Ga that can be irreversibly chelated to 1.

TABLE 3

Titration of Ga(NO$_3$)$_3$ with 1 and the amount of Ga$^{3+}$ detected by ICP-OES and $^{71}$Ga-NMR in terms of Au/Ga ratio and Ga$^{3+}$ in mg respectively.

| S. No. | Amt of Ga(NO3)3 in mg | Sample Labels | Ga 294.363- Exptl value for 25 ml diluted solution ppm | Exptl value for stock solution ppm | Au 242.794 Exptl value for 25 ml diluted solution ppm | Exptl value for stock solution ppm | calculated value Au ppm |
|---|---|---|---|---|---|---|---|
| 1 | 2.5 | P-2.5 | 0.90 | 112.83 | 14.04 | 1755.16 | 450 |
| 2 | 5.0 | P-5.0 | 0.57 | 71.65 | 12.94 | 1617.61 | 450 |
| 3 | 10.0 | P-10 | 0.04 | 5.03 | 11.20 | 1399.94 | 450 |
| 4 | 15 | P-15 | 0.01 | 1.12 | 11.28 | 1410.27 | 450 |
| 5 | 20 | P-20 | 0.02 | 2.75 | 11.53 | 1441.28 | 450 |
| 6 | 30 | P-30 | 0.32 | 39.99 | 9.90 | 1238.03 | 450 |
| 7 | 40 | P-40 | 0.23 | 29.00 | 9.41 | 1175.80 | 450 |
| 1 | 2.5 | S-2.5 | 0.20 | 25.13 | 0.10 | 11.88 | |
| 2 | 5.0 | S-5.0 | 0.37 | 45.92 | 0.10 | 12.53 | |
| 3 | 10.0 | S-10 | 2.57 | 320.88 | 0.06 | 7.91 | |
| 4 | 15 | S-15 | 4.22 | 527.21 | 0.07 | 9.24 | |
| 5 | 20 | S-20 | 5.69 | 711.13 | 0.07 | 8.55 | |
| 6 | 30 | S-30 | 9.73 | 1216.32 | 0.03 | 3.83 | |

TABLE 3-continued

Titration of Ga(NO$_3$)$_3$ with 1 and the amount of Ga$^{3+}$ detected by ICP-OES and $^{71}$Ga-NMR in terms of Au/Ga ratio and Ga$^{3+}$ in mg respectively.

| S. No. | Amt of Ga(NO3)3 in mg | Sample Labels | Ga 294.363- Exptl value for 25 ml diluted solution ppm | Exptl value for stock solution ppm | Au 242.794 Exptl value for 25 ml diluted solution ppm | Exptl value for stock solution ppm | calculated value Au ppm |
|---|---|---|---|---|---|---|---|
| 7 | 40 | S-40 | 12.82 | 1603.01 | −0.01 | −1.72 | |
| 1 | 2.5 mg/ml of construct | AuNP-DTDTPA | −0.28 | −35.44 | 27.35 | 3419.07 | 1125 |
| 2 | 20 mg/ml | Ga(NO3)3 | 42.93 | 5365.74 | 0.15 | 18.87 | 2000 |

Example 2

Synthesis of [AuNP(DTDTPA)(Peptide)] was conducted as described below. The following peptides were used.

```
                                          SEQ ID NO: 1
Peptide 1 =
Thioctic acid bombesin; Lipoic-Gln-Trp-Ala-Val-
Gly-His-Leu-Met-NH2 (Lipoic-QWAVGHLM-NH2)

SEQ ID NO: 2
Peptide 2 =
Thioctyl-Lys-Lys-Lys(DOTA)-PEG2-Tyr-His-Trp-Tyr-
Gly-Tyr-Thr-Pro-Gln-Asn-Val-Ile [Thioctyl-KKK
(DOTA)-PEG2-YHWYGYTPQNVI]
```

General Procedure:

Thioctic acid terminated peptide was reacted with gold nanoparticles with stoichiometric ratios of Au:Peptide 1:0.25, 1:0.5, 1:1, 1:2 and 1:4. Typically, in a 20 ml glass vial, a solution of AuNP-DTDTPA ([Au]=2.28 μmol) using aqueous/methanolic mixture (1:9) of 0.01M NaOH was prepared. Thioctic acid terminated peptide [0.57 μmol, 1.14 μmol, 2.27 μmol, 4.54 μmol and 9.08 μmol] were dissolved in 4 mL of MeOH and then added to the nanoparticles solution. The reaction mixture was stirred for 2 hours at room temperature and formation of a dark brown precipitate was observed. The mixture was centrifuged (9300 g for 10 min at 20° C.) and the supernatant was removed. The precipitated AuNPs were washed two times with MeOH and three times with water. The AuNP(DTDTPA)(Peptide) were dried at low pressure and stored at −20° C.

Synthesis of AuNP(DTDTPA)(Ga)(Peptide) was Conducted as Follows.

Complexation with Gallium was performed by the addition of Ga(NO3)3 to a colloidal solution of AuNP(DTDTPA)(Peptide) at room temperature with continuous stirring. The optimum content of gallium required for chelation was monitored by titrimetric analysis performed on ICP-OES and by 71Ga-NMR experiments. Typically, a solution of AuNP(DTDTPA)(Peptide) ([Au]=22 mM) was prepared using 0.01M NaOH to maintain the pH between 7 and 8. To this solution were added 118 mM of Ga(NO3)3 with continuous stirring at room temperature. The formation of precipitate was immediately observed. The reaction mixture was allowed to stir for 3 hours and a brownish black residue was collected by centrifugation. The residue was washed with DI water thoroughly to remove any unreacted gallium salt.

Synthesis of AuNP(DTDTPA)(671Ga)(Peptide) as Performed as Follows.

In a 2 mL eppendorf, 190 μL of 0.4M ammonium acetate (pH≈7) were mixed with 20 μL of AuNP(DTDTPA)(Peptide) (5 mg/mL, 0.01M NaOH). To this mixture, 250 μL of 671GaCl3 (in 0.1M HCl) were added. The solution was left at room temperature for 5 min. The solution was then filtered in a Millipore Amicon Ultra 0.5 mL 10 k. The collected AuNPs were diluted in 150 μL of H2O and their radiochemical purity assessed by ITLC-SG, using 6M HCl/MeOH (5:95) as eluent (AuNP(DTDTPA)(Peptide): Rf=0). The radiolabeling yield was 87.5% and the radiochemical purity >95%.

Synthesis of 671Ga-AuNP-DTDTPA was performed as follows. In a 2 mL eppendorf, 350 μL of 0.4M ammonium acetate (pH≈7) were mixed with 20 μL of AuNP-DTDTPA (5 mg/mL, [Au]=11.42 μmol) in 0.01M NaOH). To this mixture, 250 μL of 671GaCl3 (0.1M HCl) were added. The reaction mixture was heated at 85° C. for 15 min. The solution was then filtered in a Millipore Amicon Ultra 0.5 mL 10 k. The collected AuNPs were diluted in 150 μL of H2O and their radiochemical purity assessed by ITLC-SG, using 6M HCL/MeOH (5:95) as eluent (671Ga-AuNP-DTDTPA: Rf=0). The radiolabeling yield was 86.7% and the radiochemical purity >95%.

Figure 8:
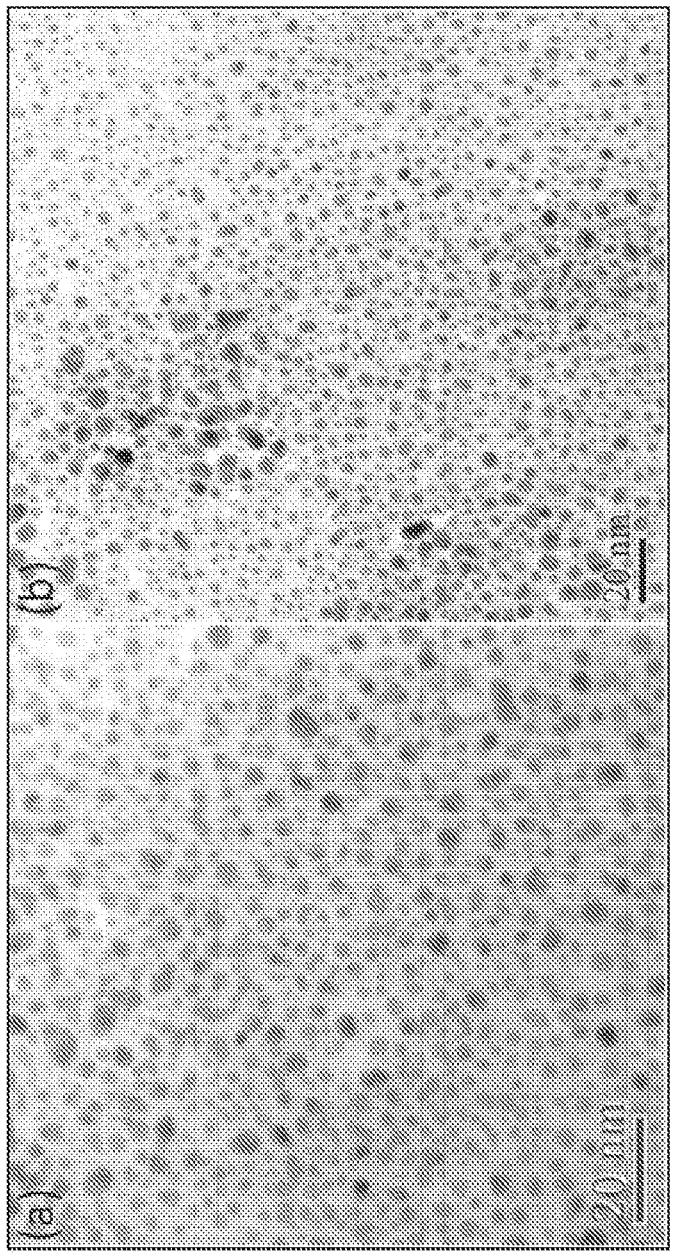
FIG. 8 is an TEM image of (a) AuNP(DTDTPA)(Peptide) and (b) AuNP(DTDTPA)(Ga)(Peptide)
Figure 9A:
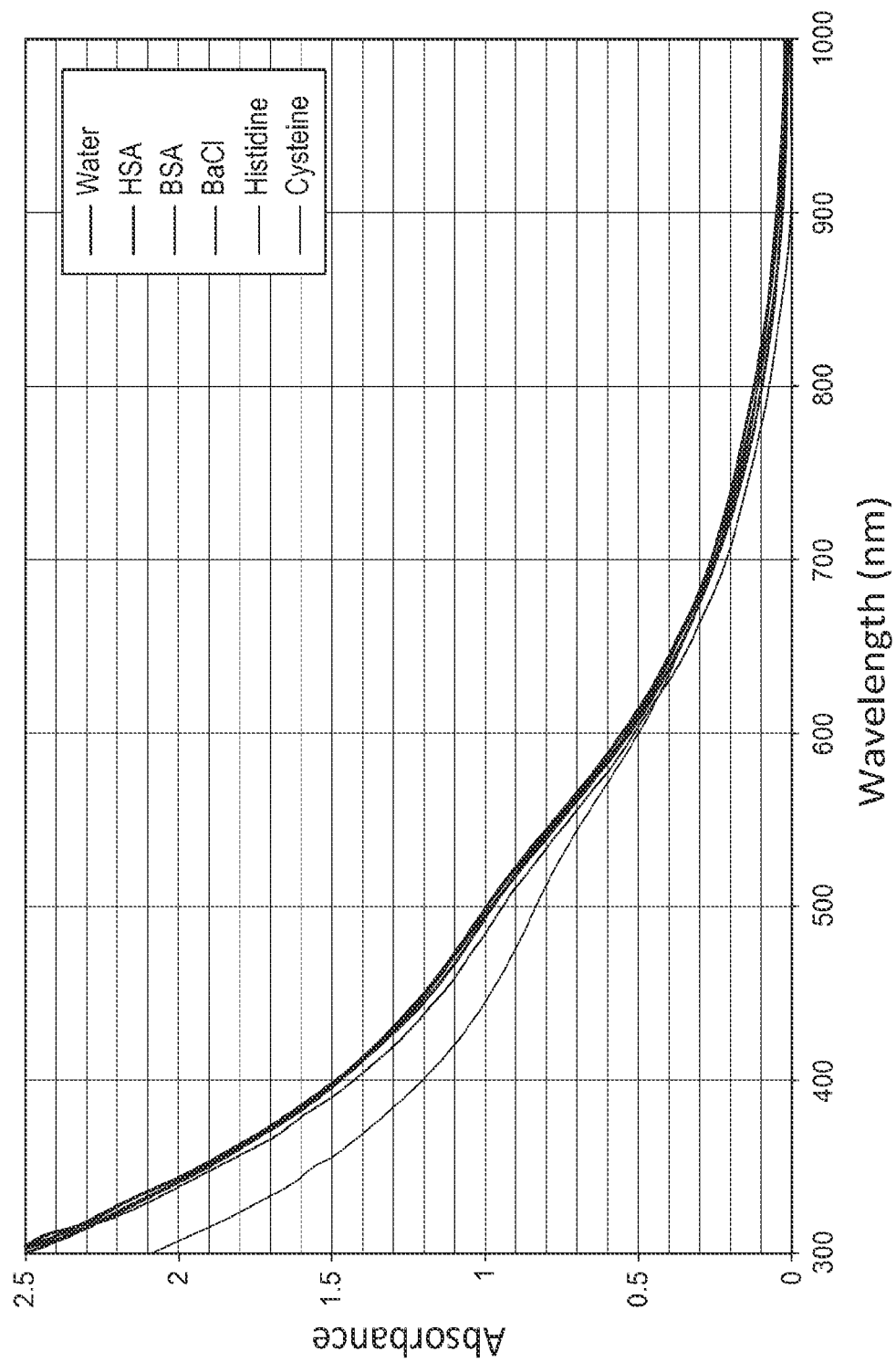
FIG. 9 is in vitro stability studies of AuNP(DTDTPA) (Peptide) and (b) AuNP(DTDTPA)(Ga)(Peptide) by UV-Visible absorption spectroscopy (A, B); by DLS size analysis (C, D); by zeta potential (E, F) in various biological solutions.
Figure 9B:
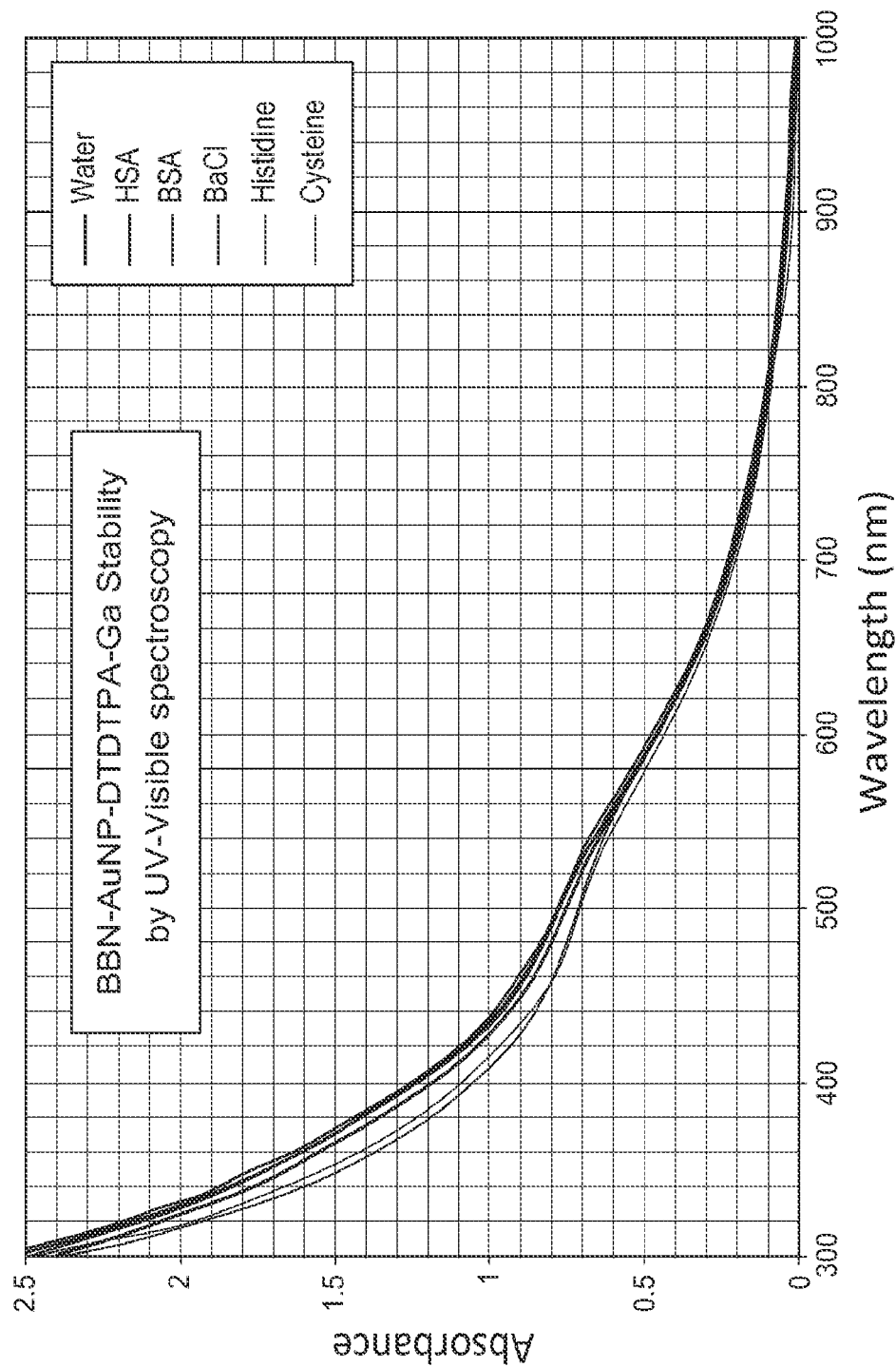
Figure 9C:
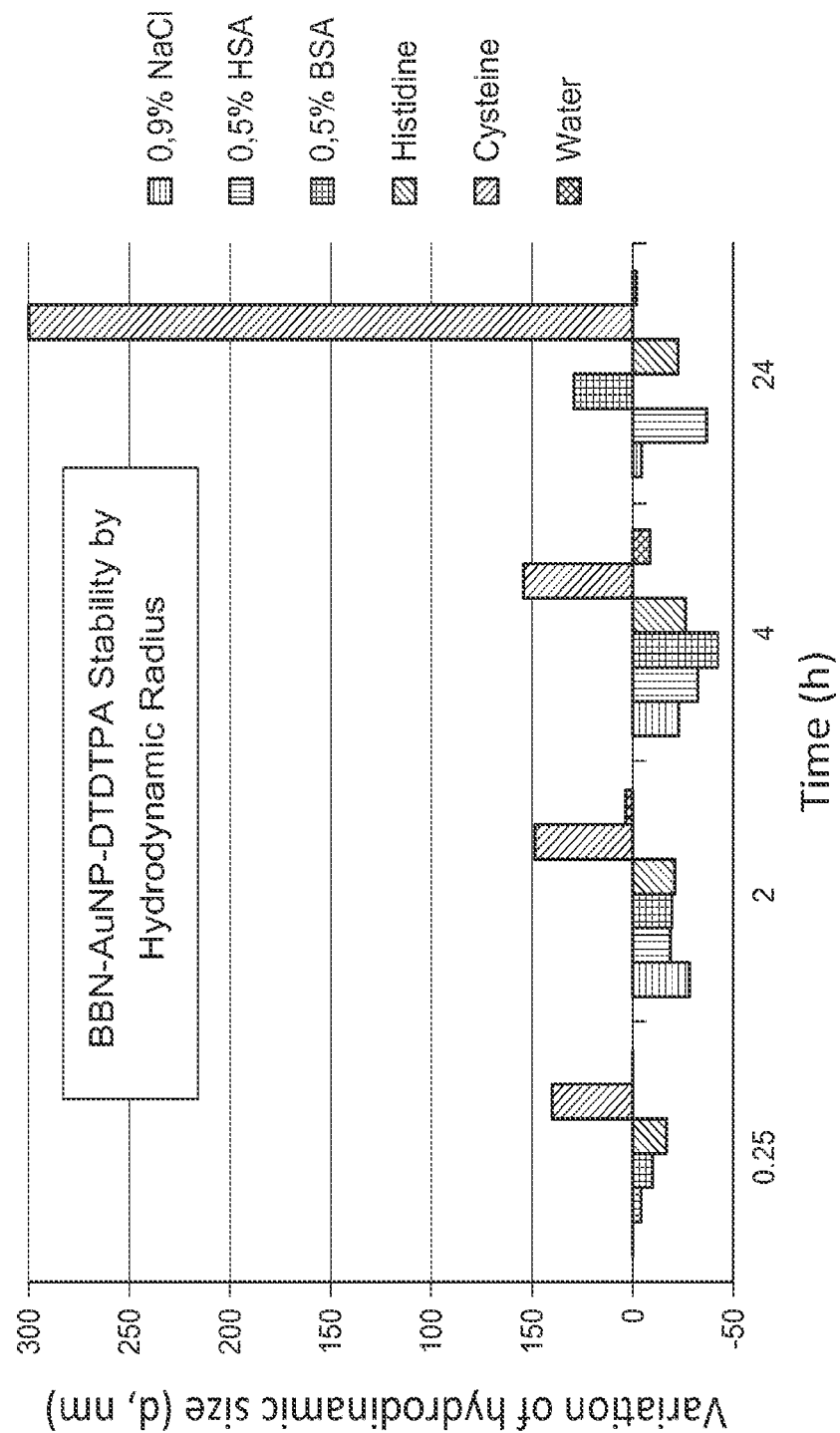
Figure 9E:
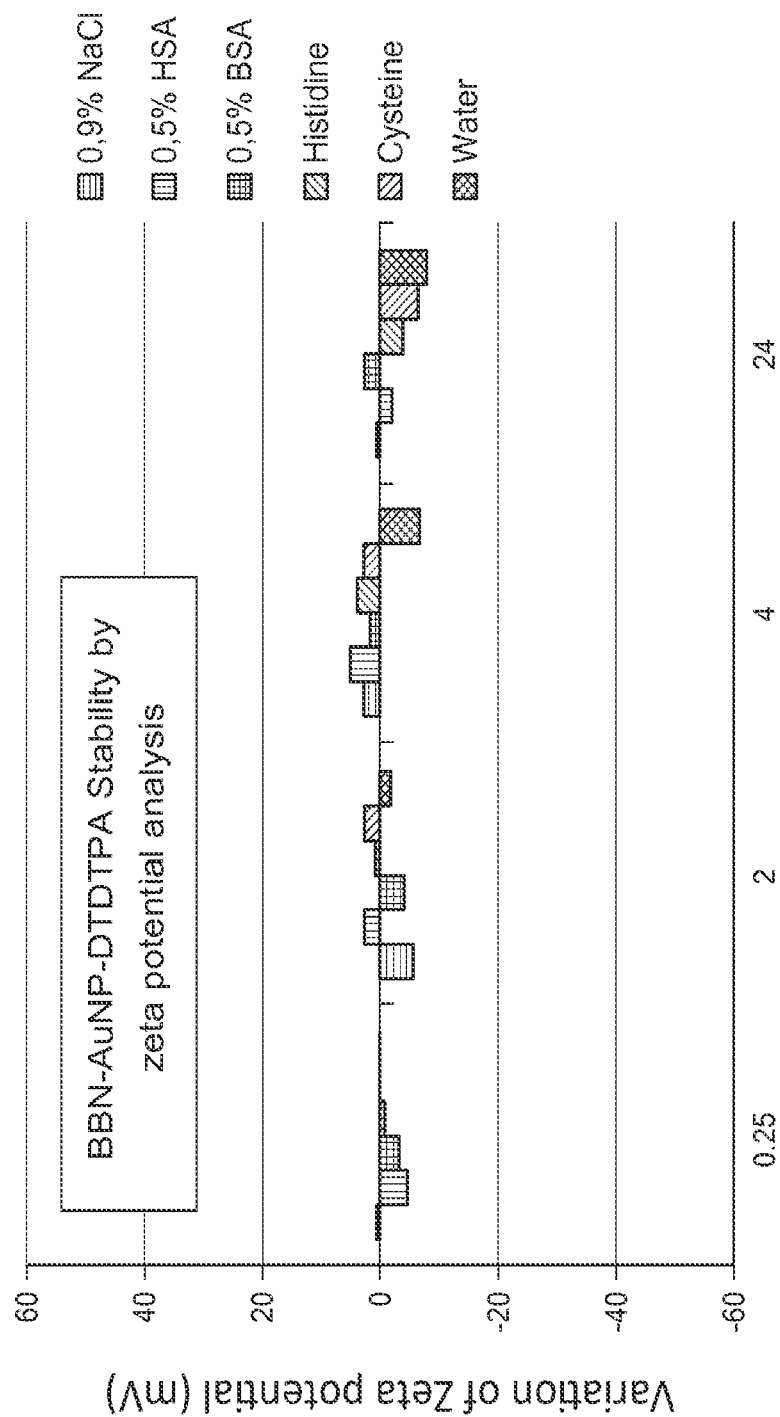
Figure 9F:
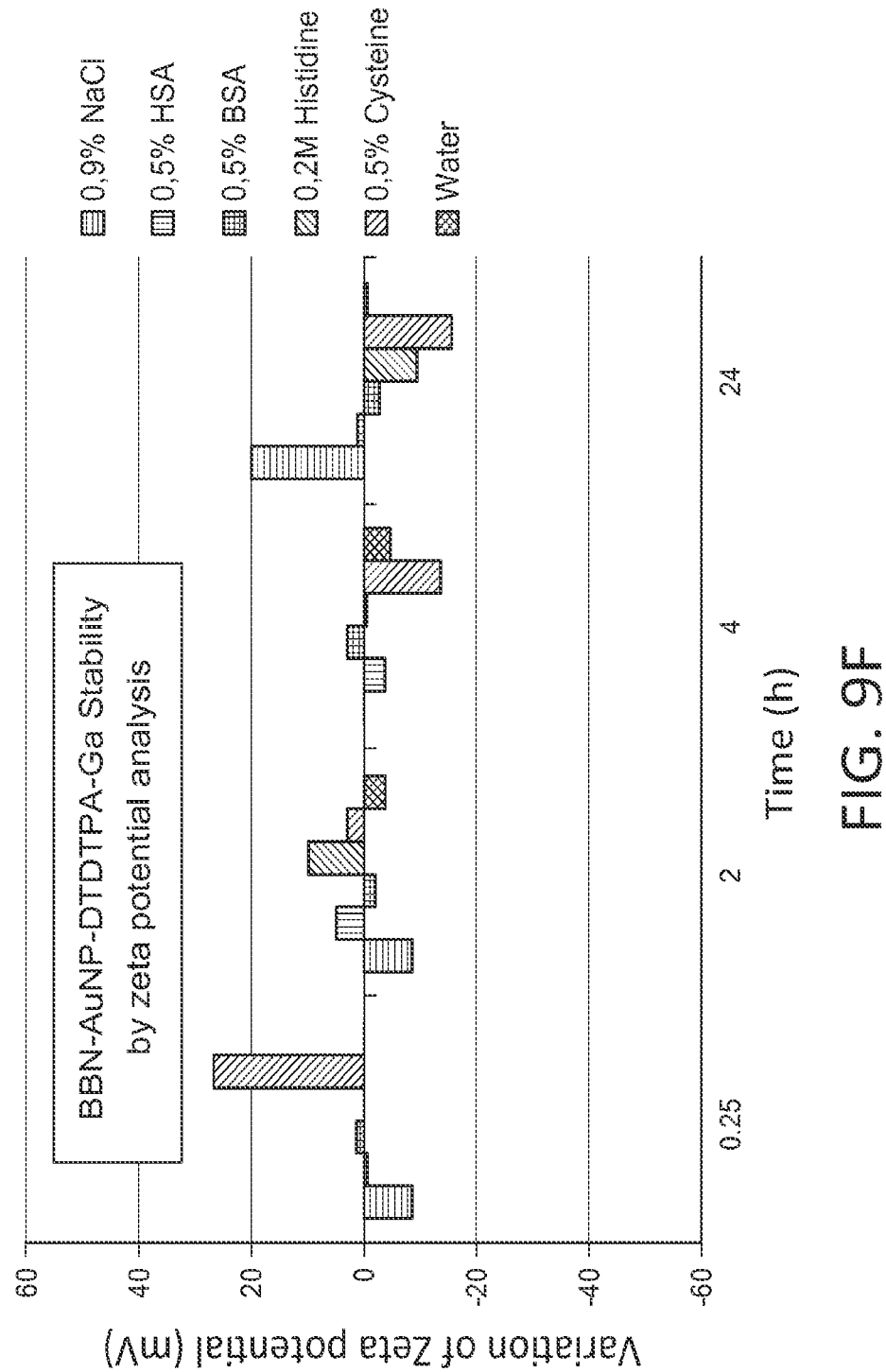

Physicochemical properties of the nanoconstructs were then studied. FIG. 8 is a micrograph of (a) AuNP(DTDTPA)(Peptide) and (b) AuNP(DTDTPA)(Ga)(Peptide). Table 4 below provides physicochemical properties of various reactions of BBN-AuNP-DTDTPA.

TABLE 4

Physicochemical properties of various reactions of BBN-AuNP-DTDTPA.

| | Size (nm) | Charge (mv) |
|---|---|---|
| Au:Peptide 1 (1:0.4) | 110 | −73 |
| Au:Peptide 1 (1:2) | 105 | −69 |
| Au:Peptide 1 (1:4) | 120 | −66 |
| [AuNP(DTDTPA)(Peptide1)] | 122 | −54 |
| AuNP(DTDTPA)(Peptide2)] | 167 | −53 |

Additional studies were conducted to evaluate in vitro stability of AuNP(DTDTPA)(Peptide) and AuNP(DTDTPA)(Ga)(Peptide). These results are presented in FIG. 9.

Figure 10A:
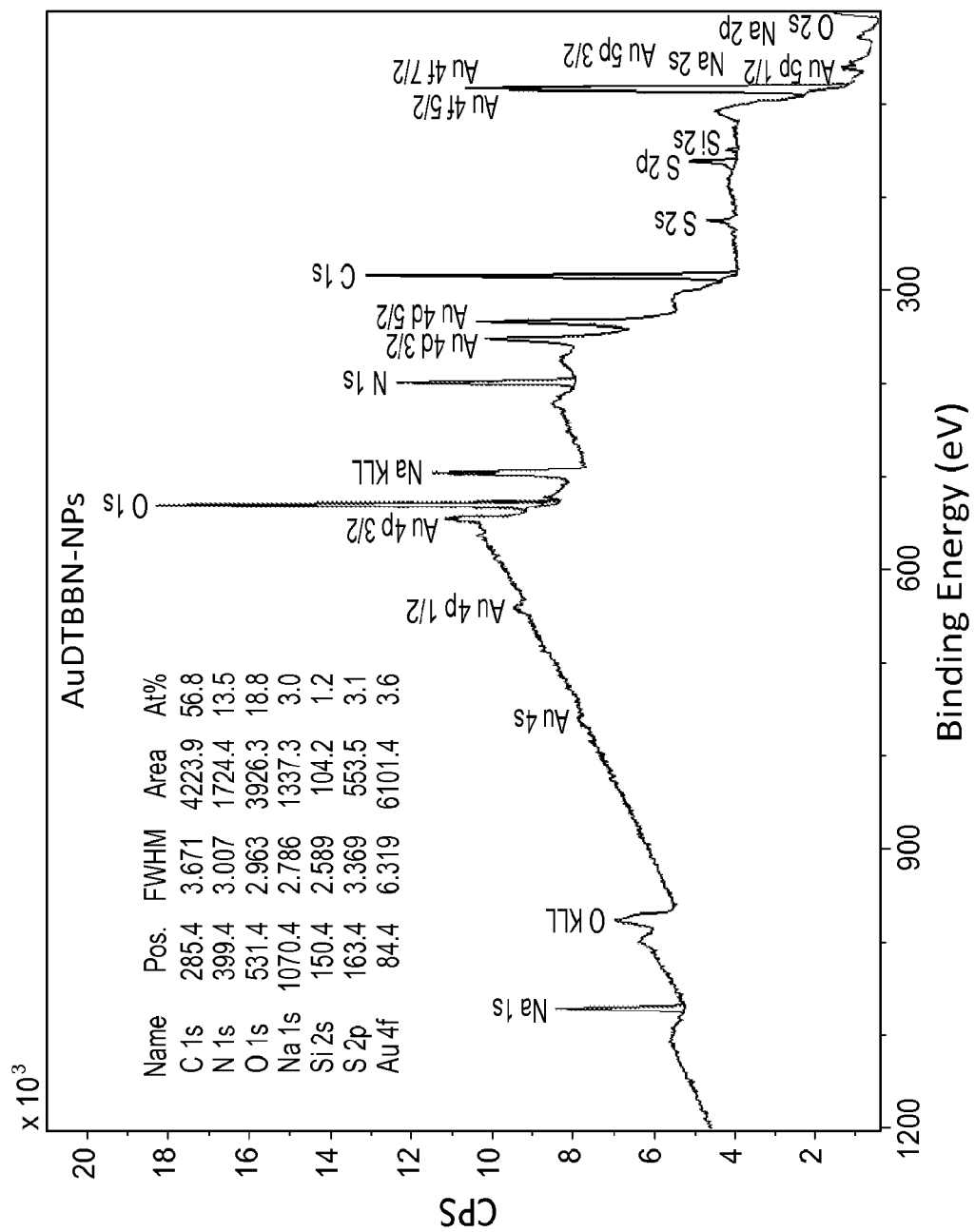
FIG. 10 is (A) XPS survey spectrum of AuNP(DTDTPA) (Peptide 1); (B) XPS hi-res spectrum of AuNP(DTDTPA) (Peptide 1), C 1s Region.
Figure 10B:
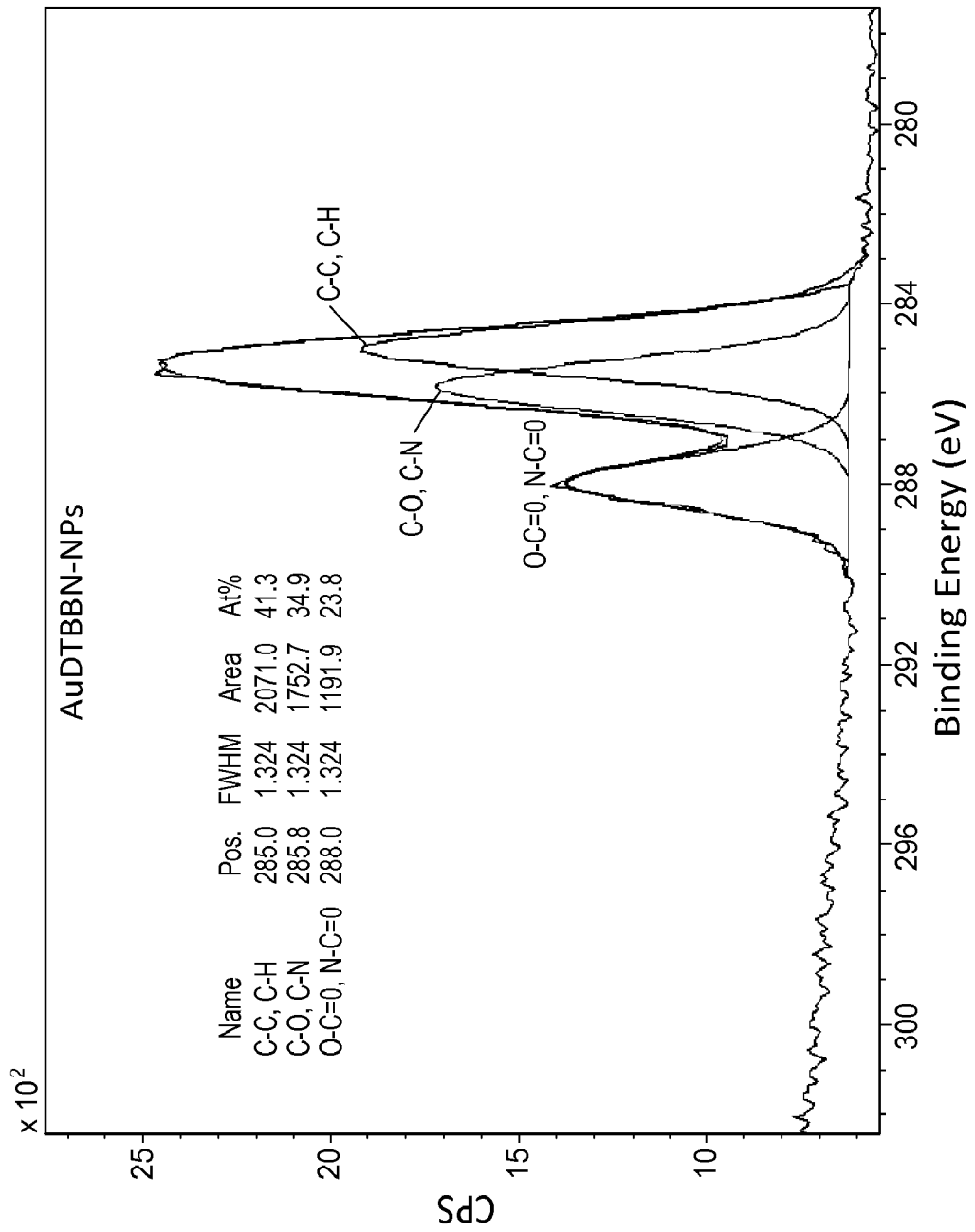

FIG. 10 provides the XPS survey spectrum of AuNP(DTDTPA)(Peptide 1).

Figure 11A:
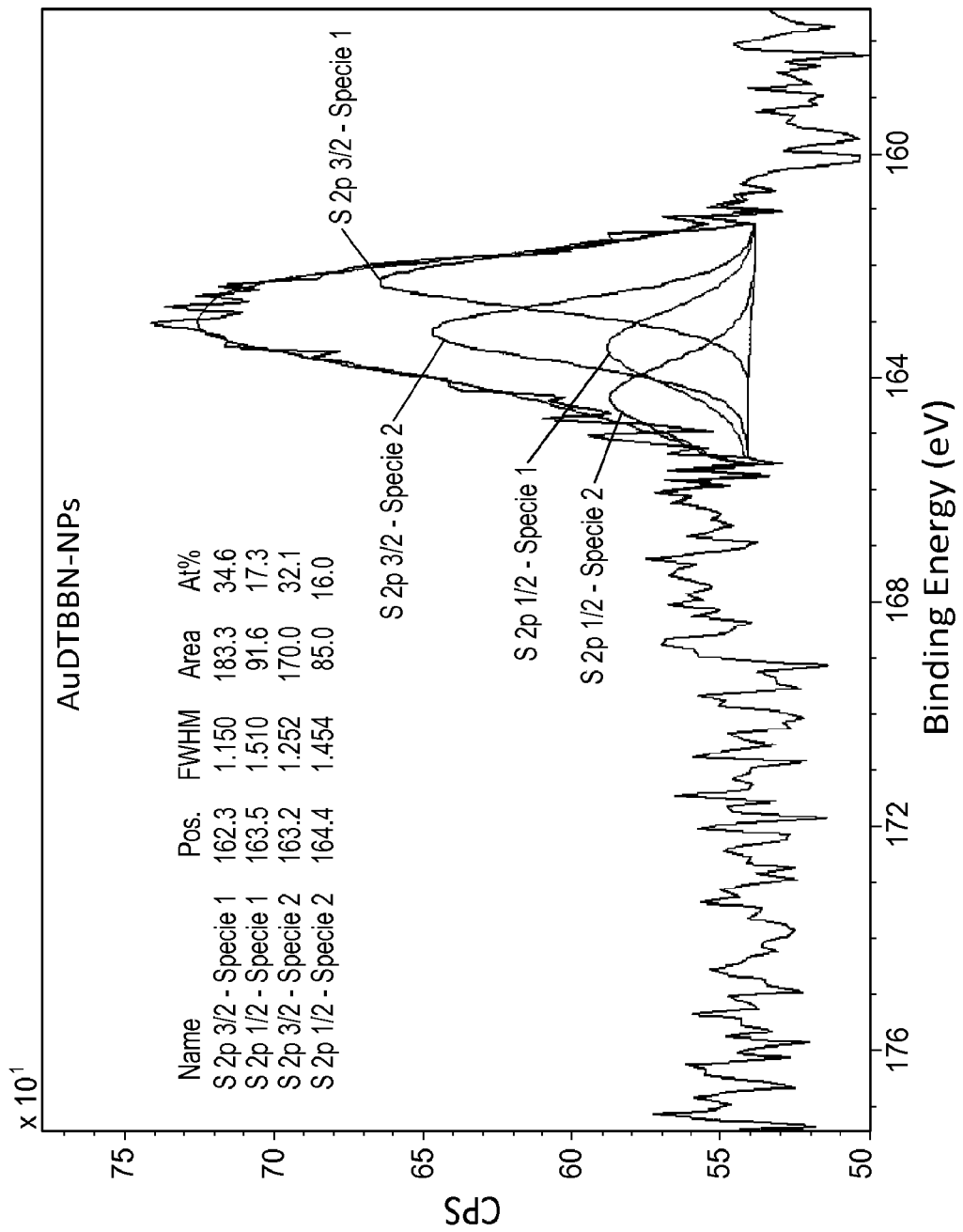
FIG. 11 is (A) XPS hi-res spectrum of AuNP(DTDTPA) (Peptide 1), S 2p Region; (B) XPS hi-res spectrum of AuNP(DTDTPA)(Peptide 1), Au 4f Region.
Figure 11B:
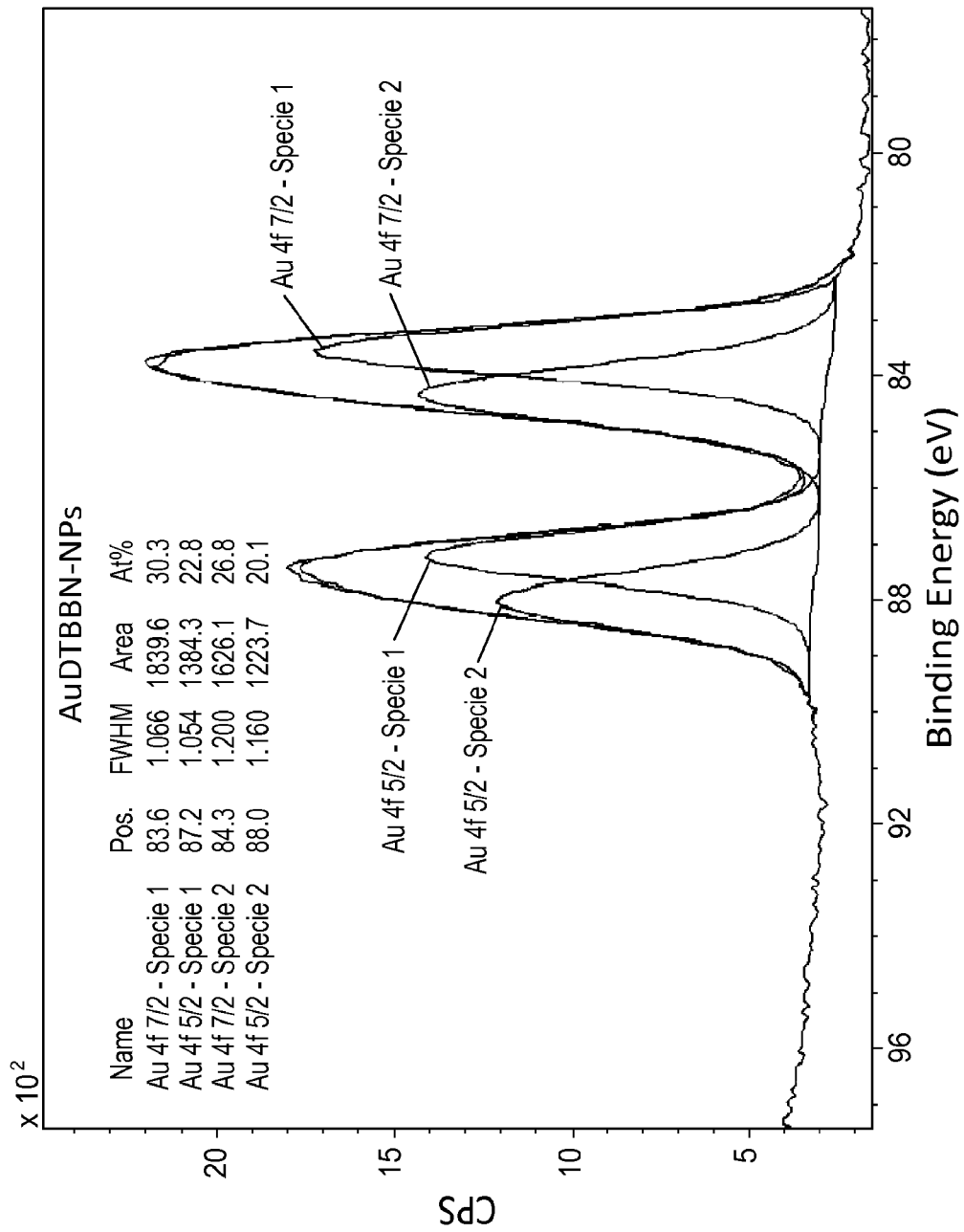

FIG. 11 provides the XPS hi-res spectrum of AuNP (DTDTPA)(Peptide 1).

Table 5 reports the relative elemental composition for AuNP(DTDTPA)(Peptide 1)

TABLE 5

Relative Elemental Composition of AuDTBBN-NPs as Determined by XPS [Atom %]

|  | C | N | O | Na† | Si* | S | Au |
|---|---|---|---|---|---|---|---|
| AuNP(DTDTPA) (Peptide1) | 57 | 14 | 19 | 3.0 | 1.2 | 3.1 | 3.6 |

†Sodium detected due to dissolution in NaOH solution
*Silicon detected due to deposition on silicon wafer Table 6 report relative compositions and most probable peak assignments for carbon species.

TABLE 6

Relative Compositions and Most Probable Peak Assignments for Carbon Species as Determined by XPS, C 1s Region [Atom %]

|  | C—C, C—H | C—O, C—N | O—C=O, N—C=O |
|---|---|---|---|
| AuNP(DTDTPA)(Peptide1) | 41 | 35 | 24 |

As shown in FIG. 11, the analysis of the XPS hi-res spectrum for the S 2p region suggests that there are two different S states for the sample. The energies for elemental S, and some organic forms of S fall in the range of 163-164 eV [1], which corresponds to the 163.2 eV peak energy listed as Specie 2. This is likely S that is NOT bound to the Au. There is also a S peak (Specie 1) at 162.3 eV, which corresponds to the peak energy reported for S—Au bonding [2]. The peak energy of 84.3 eV for the Au 4f7/2 peak labeled Specie 2 suggests that the Au is bound to S [1], though this energy is slightly lower than the tabulated value. If not for the evidence of Au—S bonding from the S 2p hi-res it might be believed that this peak was due to Au—N [3]. The sample also contains a peak at 83.6 eV, which is likely due to Au in the metallic form, not bound with the organic material in any manner.

Figure 12:
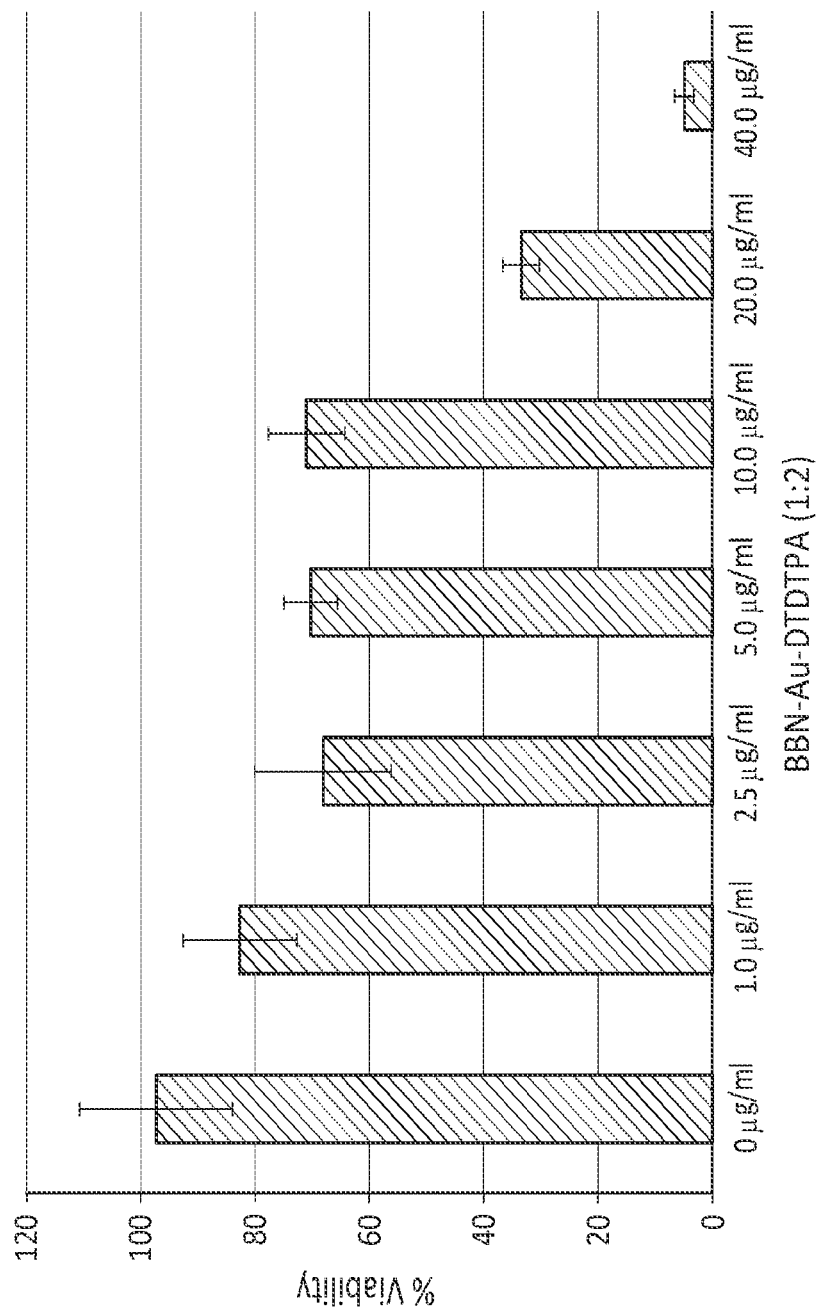
FIG. 12 is a dose-dependent MTT cytotoxicity assay of AuNP(DTDTPA)(Peptide 1) (1:2) in PC-3 prostate cancer cells.

A dose dependent cytotoxicity assay with AuNP(DTDTPA)(Peptide 1) was also conducted in PC-3 prostate cancer cells. The results of this assay are reported in FIG. 12.

While specific embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the appended claims.

The invention claimed is:

1. A multicomponent nanomaterial comprising AuNP (DTDTPA)(Ga)(biomolecule), wherein DTDTPA is dithiolated diethylenetriamine pentaacetic acid, wherein DTDTPA is linked to the surface of the Au nanoparticle (NP) via an Au—S bond, and wherein the biomolecule is Thioctyl-KKK(DOTA) PEG2-YHWYGYTPQNVI.

2. The multicomponent nanomaterial of claim 1, wherein Au and Ga are present in an Au:Ga ratio ranging from 1:5 to 1:1.125.

3. The multicomponent nanomaterial of claim 2, wherein the ratio of Au:Ga is 1:5.

4. The multicomponent nanomaterial of claim 1, wherein the Ga comprises Ga-67.

5. The multicomponent nanomaterial of claim 1, wherein the Ga comprises Ga-68.

6. A solution comprising the multicomponent nanomaterial of claim 1, wherein the solution has a pH ranging from 6 to 13, and wherein the multicomponent nanomaterial is present in the solution in a concentration ranging from 30 µg/ml to 5 mg/ml.

7. A method for synthesizing the multicomponent nanomaterial of claim 1, the method comprising:

mixing an aqueous solution comprising a biomolecule, wherein the biomolecule is Thioctyl-KKK(DOTA)-PEG2-YHWYGYTPQNVI, with Ga(NO$_3$)$_3$;

adding AuNP(DTDTPA) dissolved in buffer at room temperature to the aqueous solution to form a mixed solution, wherein DTDTPA is dithiolated diethylenetriamine pentaacetic acid; and continually stirring the mixed solution until AuNP(DTDTPA)(Ga)(biomolecule) nanoparticles are formed.

8. A method for synthesizing the multicomponent nanomaterial of claim 1, the method comprising:

mixing an aqueous solution comprising a biomolecule, wherein the biomolecule is Thioctyl-KKK(DOTA)-PEG2-YHWYGYTPQNVI, with AuNP(DTDTPA) dissolved in buffer at room temperature to form a mixed solution, wherein DTDTPA is dithiolated diethylenetriamine pentaacetic acid;

stirring the mixed solution to form AuNP(DTDTPA)(biomolecule); and adding Ga(NO$_3$)$_3$ and stirring until AuNP(DTDTPA)(Ga)(biomolecule) nanoparticles are formed.

* * * * *